United States Patent [19]
Olsen et al.

[11] Patent Number: 6,031,152
[45] Date of Patent: Feb. 29, 2000

[54] PROMOTER FROM A LIPID TRANSFER PROTEIN GENE

[76] Inventors: Odd-Arne Olsen, Tarnveien 16, 1430 As, Tarnvein, Norway; Roger Kalla, 3 Mowle Place, Weetangera A.C.T., 2614, Australia; Casper Linnestad, Overe Linnestad N-1540, Vestby, Norway

[21] Appl. No.: 08/702,609

[22] PCT Filed: Feb. 23, 1995

[86] PCT No.: PCT/NO95/00042

§ 371 Date: Nov. 20, 1996

§ 102(e) Date: Nov. 20, 1996

[87] PCT Pub. No.: WO95/23230

PCT Pub. Date: Aug. 31, 1995

[30] Foreign Application Priority Data

Feb. 24, 1994 [GB] United Kingdom ............. 9403512

[51] Int. Cl.[7] .............. A01H 1/00; A01H 5/10; C12N 5/10; C12N 15/82
[52] U.S. Cl. ............. 800/205; 800/235; 800/250; 435/69.1; 435/320.1; 435/410; 435/412; 435/419; 435/468; 536/24.1
[58] Field of Search .............. 435/69.1, 172.1, 435/172.3, 320.1, 410, 412, 419; 536/23.1, 23.7, 24.1; 800/205, 235, 250

[56] References Cited

U.S. PATENT DOCUMENTS 5,525,716  6/1996  Olsen et al. ............. 536/24.1

OTHER PUBLICATIONS

Fleming, A., The Plant Journal, 2: 855–862 (1992).
Gausing, K., Planta 192: 574–580 (1994).
Linnestad, C., et al., Plant Physiol. 97: 841–843 (1991).
Olsen, O.A., et al., J. Cell Biochem. Suppl. 0, 18 part A, p. 99 (1994).
Skriver, K., et al., Plant Molecular Biology 18: 585–589 (1992).
Sossountzov, L., et al., Plant Cell 3: 923–933 (1991).

*Primary Examiner*—David Guzo
*Attorney, Agent, or Firm*—St. Onge Steward Johnston & Reens LLC

[57] ABSTRACT

An expression system for at least the aleurone cells of a developing caryopsis or for at least the scutellar epithelial tissue or vascular tissue of a germinating seedling or developing grain or plant (e.g. in the root, leaves and stem) is described. The expression system comprises a gene promoter fused to a GOI (gene of interest). In a preferred embodiment the expression system comprises the GOI fused to a modified Ltp1 promoter.

23 Claims, 11 Drawing Sheets

FIG. 3

```
  1  GAGCTCCAAG GCATCACCAA GCTTCTATGA CGCCAAAACA TCCAAGAAAG ATATGTACTA GGATACCAAG CACCC
 76  AAGAGTAAAC GGAGGAAGTA TAATATAAGG CCCTGTTTGA TAACAAAGTA GTAAAAAAAC TAAAGTATTA AAAAC
151  TGCAGTAATT TTACGTGTAG ATAGAAAAATA CCATGGTTTT AATATAATAA TATTTTTTGC AGTATTCACA ATGTA
226  GAGAAACTGT TTGATTACGC CACATATTAC TGCAGTTTAG ATCGAGCAAG TACACGGGAA GAAGATAACG ACGTC
301  CCACCCCTTC TTTTCGCCTT CTCTGTTTTT TAAAAAGAGG TCTGGGGTTA GTTTTTTCAA TACTGCAGTT TTAAA
376  ATCACAATTC TTAGAGGCAA CCAAACACCT CATTGTAAAT AAAAACTATGA TAATCTCCAA AACTGCAGTA TTCTA
451  AAAATACTAC AAAAATTCTT TGTTATCAAA CAGGGCCTAA GGAGTTAAAA AAATTTAGCC GTAACTGAGA CTCGG
526  CGAGGCACCA GCAGCTAGCA GTCATCAACA CTTGATGGTT GGCAAAGGCG AGTCGACGTG TCGCGGGGCT CGGCC
601  TGAGCGGGAG ATACAATCTG TTCTCCAGTA ACCCCGTCGA TTTGGCCCGC CGACTAAAGC ATCCAGCAT CTCTC
676  GCTCGAACCC CTATTTAAGC CCCTCCATTC CTCCCAACAT TCTCCACACC TCCACGAGTT GCTCATCACT AGCTA
751  GTACGTTGTA CTGTTAGCTA CAGATTAAGA AGTGATC ATG GCC CGC GCT CAG GTA CTG CTC ATG
                                                  M   A   R   A   Q   V   L   L   M

815  GCC GCC GCC TTG GTG CTG ATG CTC ACG GCG GCC CCG CGC GCT GCC GTG GCC CTC AAC
      A   A   A   L   V   L   M   L   T   A   A   P   R   A   A   V   A   L   N

872  TGC GGC CAG GTT GAC AGC AAG ATG AAA CCT TGC CTG ACC TAC GTT CAG GGC GGC CCC
      C   G   Q   V   D   S   K   M   K   P   C   L   T   Y   V   Q   G   G   P
```

FIG. 3 Continued

```
929  GGC CCG TCC GGC GAA TGC TGC AAC GGC GTC AGG GAT CTC CAT AAC CAG GCG CAA TCC
     G   P   S   G   E   C   C   N   G   V   R   D   L   H   N   Q   A   Q   S

986  TCG GGC GAC CGC CAA ACC GTT TGC AAC TGC CTG AAG GGG ATC GCT CGC GGC ATC CAC
     S   G   D   R   Q   T   V   C   N   C   L   K   G   I   A   R   G   I   H

1048 AAT CTC AAC CTC AAC AAC GCC GCC AGC ATC CCC TCC AAG TGC AAT GTC CCA
     N   L   N   L   N   N   A   A   S   I   P   S   K   C   N   V   P

1100 TAC ACC ATC AGC CCC GAC ATC GAC TGC TCC AG gtgattaaat ttacactcat ccagagtgaa at
     Y   T   I   S   P   D   I   D   C   S   R 1164 ctttaaaaag aactatattt acgaacggag tgagtatata ggaacattca tccacgtaaa atttgttgat attaa 1240 cattaacacg catgattgac ctgcag G ATT TAC TGAGCGACGA TCCGTCAAGC TGGTGCTCAG CTCATCGA
                                 I   Y   *

1310 TCCACGTGGA GCTGAAGCGC GCAGCCTCTG TCCCTATGTA GTATGGCTAC CAGTTATGCC GAGTTTATGC TGAAT

1385 AAGAACTCTC TCCTGTACTC CTTTGGAGGA GATCAGTATC TATGTACGTG AGAGTTGAGA GTTTGTACCA TCGGC

1460 ACTCCCAGTG TTTATGGACT ATATGCAT
```

FIG. 4

```
GTCCACAACTC ATGAGCATCA CGGAATGGCA TGAGTTGAAA TATAACTACA TTGCTCAAA   -1621
GCAACAAAAAG CACATTAGAA TCTTGAGCAT TGAGATAAGA GTTTTTCTCA TGCTCTAAA   -1561
TATATATTTTG AGAATCCTTT GGAGGAGAAA AATCCATATT TACAATTCGT TGTAAATTT   -1501
GAGTCCATGAT CCTAAAGAGA TTAAGCATGC GAATTACCCA AACATCAAAA TTTGTGCCA   -1441
TTGAAACTAAG AGTGTTAGAG AATCCTAATC CCCTAGTTGA CATACTTACT CTCTAGGTG   -1381
GTGAAACCTAA TAATGAGAGA TCTAGCTCTA ATACCAATTG AGAGGATGTG GATGTCGCC   -1321
TAGAGGGGCGG TGAATAGGCG CTTTAAAATA ATTACGGTTT AGGCTCGAAC AAATGTGGA   -1261
ATAAAACTAAC GTTTCATTTG TCAAGCGCAA AACCTAAAAC AACTAAGTGA TGGCAGAATA   -1201
CACCAACAACT TATGATAAGC AAGATAAAAA AACTAAGTGA TGGCAGAATA TATAACAAG   -1141
AAACAATATGG CTATCACAAA GTGAAGTGCA TAAGTAAACA GCTCGGGTAA GGGACAACC   -1081
GAGCCATGCGG AGACGACGAT GTATCCCTCAA GTTCACACAC TTGCGGATGC TAATCTCCG   -1021
TTTGAAGCAGT GTGGAGGCAC AATCGTCCCC AAGAAGCCAC TAAGGCCACC GTAATCTCC    -961
TCACGCCCTCG CACAATCGAA GATGTTGTGA TTCCACTAAG GGACCCTTGA GGGCAGTCA    -901
CTGAACCCGTA TAAACATGGT TGGAACAATC TCCACGACTT AATTGGAGAC TCCCAACAA    -841
CACCACGAACC TTCATCATAA CGAAATATGG CTTCGAGGTA ACCTCAAATG CTCGGGGCA    -781
ATTTTTACAAC CTAATTGAAG ACCTCGACGC TTGCGTGGAG CTTTACACTA TAATGATTG    -721
AGCTCCAAGGG CATCACCAAG CTTCTATGAC GCCAAAAACAT CCAAGAAAGA TATGTACTA    -661
```

FIG. 4 Continued

```
GGATACCAAGC ACCCAAGAGT AAACGGAGGA AGTATAATAT AAGGCCCTGT TTGATAACA   -601
AAGTAGTAAAA AAACTAAAGT ATTAAAAACT GCAGTAATTT TACGTGTAGA TAGAAAATA   -541
CCATGGTTTTA ATATAATAAT ATTTTTTGCA GTATTCACAA TGTAGAGAAA CTGTTTGAT   -481
TACGCCACATA TTACTGCAGT TTAGATCGAG CAAGTACACG GGAAGAAGAT AACGACGTC   -421
CCACCCCTTCT TTTCGCCTTC TCTGTTTTTT AAAAAGAGGT CTGGGGTTAG TTTTTTCAA   -361
TACTGCAGTTT TAAAATCACA ATTCTTAGAG GCAACCAAAA CACCTCATTG TAAATAAAAC   -301
TATGATAATC TCCAAAACTG CAGTATTCTA AAAATACTAC AAAAATTCTT TGTTATCAAA   -241
CAGGGCCTAA GGAGTTAAAA AAATTTAGCC GTAACTGAGA CTCGGCGAGG CACCAGCAGC   -181
TAGCAGTCAT CAACACTTGA TGGTTGGCAA AGGCGAGTCG ACGTGTCGCG GGGCTCGGCC   -121
TGAGCGGGAG ATACAATCTG TTCTCCAGTA ACCCCGTCGA TTTGGCCCGC CGACTAAAGC   -61
ATCCAGGCAT CTCTCGCTCG AACCCCTATT TAAGCCCCTC CATTCCTCCC AACATTCTCC   1
ACACCTCCAC GAGTTGCTCA TCACTAGCTA GTACGTTGTA CTGTTAGCTA CAGATTAAGA   60
AGTGATCATG GCC CGC GCT CAG GTA CTG CTC ATG GCC GCC TTG GTG CTG ATG CTC AC   120
            M   A   R   A   Q   V   L   L   M   A   A   L   V   L   M   L   T
GGCG GCC CCG CGC GCT GCC GTG GCC CTC AAC TGC GGC CAG GTT GAC AGC AAG ATG AAA CC   180
 A    A   P   R   A   A   V   A   L   N   C   G   Q   V   D   S   K   M   K   P
```

FIG. 4 Continued

```
TTGC CTG ACC TAC GTT CAG GGC GGC CCC GGC CCG TCC GGC GAA TGC TGC AAC GGC GTC AG    240
  C    L   T   Y   V   Q   G   G   P   G   P   S   G   E   C   C   N   G   V   R
GGAT CTC CAT AAC CAG GCG CAA TCC TCG GGC GAC CGC CAA ACC GTT TGC TGC AAC TGC CTG AA  300
  D    L   H   N   Q   A   Q   S   S   G   D   R   Q   T   V   C   C   N   C   L   K
GGGG ATC GCT CGC GGC ATC CAC AAT CTC AAC AAC GCC GCC AGC ATC CCC TCC AA              360
  G    I   A   R   G   I   H   N   L   N   N   A   A   S   I   P   S   K
GTGC AAT GTC AAC GTC CCA TAC ATC AGC CCC GAC ATC GAC TGC TCC AGg tgattaaa            420
  C    N   V   N   V   P   Y   I   S   P   D   I   D   C   S   R
TTTACACTCA TCCAGAGTGA AATCTTTAAA AAGAACTATA TTTACGAACG GAGTGAGTAT                    480
ATAGGAACAT TCATCCACGT AAAATTTGTT GATATTAACA TTAACACGCA TGATTGACCT                    540
GCAGGATTTA CTGAGCGACG ATCCGTCAAG CTGGTGCTCA GCTCATCGAT CCACGTGGAG                    600
           I   Y
CTGAAGCGCG CAGCCTCTGT CCCTATGTAG TATGGCTACC AGTTATGCCG AGTTTATGCT                    660
GAATAAGAAC TCTCTCCCTGT ACTCCTTTGG AGGAGATCAG TATCTATGTA CGTGAGAGTT                   720
GAGAGTTTGT ACCATCGGCA CTCCCAGTGT TTATGGACTA TATGCATACA CCTCCTTCTG                    780
TGCTCAGTGT GTAACTTGTC TCTCTGTTTC CTCACGTTCG CGTCTCATAT AATAATTTAC                    840
```

FIG. 4 Continued

```
TTATGTGCTC TAGGATCGTA GTACAGTATC ATATATATAC CTCTCTATGA ATTAGTTTAC      900
CGTAGACCGT ATGTTTCTTG AATCTGGATG AAAATTACGG ATTCAAGCGT GCGTCCCGCA      960
TATAATAAGC TTGCTTACGG ATTCAAGCGT GCGTCACGCG GCTCAGTAGA TGATGAGGAT     1020
ACTCGCTGCT GCATCTCTAC ATCCCGCTCA TGAGCTGAGC TGAGCCCGGG TCCTCCCCCG     1080
CTCCGGCCCG CTGGCCACCC CGGCCGGCCG ACCCTCAAAC AGCCTTCATG ACGAGCCGCC     1140
CGCCAGCAAG ATCTGTTGGC TCCTCCCCTG TCCGTCGTAG AGAAACCCAGC GCA           1192
```

FIG. 5

```
  1 GAGCTCCAAG GCATCACCAA GCTTCTATGA CGCCAAAACA TCCAAGAAAG ATATGTACTA GGATACCAAG CACCC
 76 AAGAGTAAAC GGAGGAAGTA TAATATAAGG CCCTGTTTGA TAACAAAGTA GTAAAAAAAC TAAAGTATTA AAAAC
151 TGCAGTAATT TTACGTGTAG ATAGAAAATA CCATGGTTTT AATATAATAA TATTTTTTGC AGTATTCACA ATGTA
226 GAGAAACTGT TTGATTACGC CACATATTAC TGCAGTTTAG ATCGAGCAAG TACACGGGAA GAAGATAACG ACGTC
301 CCACCCCTTC TTTTCGCCTT CTCTGTTTTT TAAAAAGAGG TCTGGGGTTA GTTTTTTCAA TACTGCAGTT TTAAA
376 ATCACAATTC TTAGAGGCAA CCAAACACCT CATTGTAAAT AAAAACTATGA TAATCTCCAA AACTGCAGTA TTCTA
451 AAAATACTAC AAAAATTCTT TGTTATCAAA CAGGGCCTAA GGAGTTAAAA AAATTTAGCC GTAACTGAGA CTCGG
526 CGAGGCACCA GCAGCTAGCA GTCATCAACA CTTGATGGTT GGCAAAGCCG AGTCGACGTG TCGCGGGGCT CGGCC
601 TGAGCGGGAG ATACAATCTG TTCTCCAGTA ACCCCGTCGA TTTGGCCCGC CGACTAAAGC ATCCAGGCAT CTCTC
676 GCTCGAACCC CTATTTAAGC CCCTCCATTC CTCCAACCAT TCTCCACACC TCCACGAGTT GCTCATCACT AGCTA
751 GTACGTTGTA CTGTTAGCTA CAGATTAAGA AGTGATC
```

PROMOTER FROM A LIPID TRANSFER PROTEIN GENE

This application is a 371 of PCT/NO95/00042, filed Feb. 23, 1995.

The present invention relates to a promoter and to a construct comprising the same.

In particular the present invention relates to the use of a promoter for the expression of a gene of interest (GOI) in a specific tissue or tissues of a plant.

More in particular the present invention relates to a modified promoter for a lipid transfer protein (Ltp) gene known as the Ltp1 gene. The present invention also relates to the application of this modified Ltp1 gene promoter to express a GOI in a specific tissue or specific tissues of a plant. For example, expression can be in either the aleurone layer or the scutellar epithelial layer of a monocotyledon, especially a transgenic cereal caryopsis (or grain), more especially a developing transgenic cereal caryopsis (or grain). Particular examples include expression in the scutellar epithelial tissue or vascular tissue of a transgenic rice plant, in particular in the vascular bundles and tip of emerging shoots and roots, leaf veins and vascular bundles of stems.

A diagrammatic illustration of a developing caryopsis (or grain) is presented in FIG. 1. which is discussed in detail later. In short, a typical developing caryopsis (or grain) comprises an endosperm component and an embryo component. The endosperm, which is the site of deposition of different storage products such as starch and proteins, supports the growth of the emerging seedling during a short period of time after germination. The embryo gives rise to the vegetative plant. These components and aspects are further discussed in Bosnes et al. 1992 and Olsen et al. 1992.

The embryo component can be divided into a scutellum and an embryo axis. The scutellum can be sub-divided into an epithelial layer, which is usually one cell thick, and an inner body of parenchyma cells. Likewise, the embryo axis can be subdivided into a root component and a shoot component.

The endosperm component of mature grains can be divided into a peripheral layer of living aleurone cells surrounding a central mass of non-living starchy endosperm cells. The aleurone layer in barley is three cells thick. During caryopsis germination, the cells of the aleurone layer produce amyolytic and proteolytic enzymes that degrade the storage compounds into metabolites that are taken up and are used by the growing embryo.

Two aspects of aleurone cell biology that have been intensively studied are the genetics of anthocyanin pigmentation of aleurone cells in maize (McClintock, 1987) and the hormonal regulation of gene transcription in the aleurone layer of germinating barley caryopsis (Fincher, 1989). Using transposon tagging, several structural and regulatory genes in the anthocyanin synthesis pathway have been isolated and characterized (Paz-Ares et al., 1987; Dellaporta et al., 1988). In barley, α-amylase and β-glucanase genes that are expressed both in the aleurone layer and embryos of mature germinating caryopsis have been identified (Karrer et al., 1991; Slakeski and Fincher, 1992). In addition, two other cDNAs representing transcripts that are differentially expressed in the aleurone layers of developing barley grains have been isolated. These are CHI26 (Lea et al., 1991) and pZE40 (Smith et al., 1992).

None of these references discloses expression of those gene products in specific cell types of developing grains of transgenic cereal plants or in the scutellar epithelial tissue or vascular tissue of a germinating rice seedling or a developing rice grain or rice plant.

In the life of a developing caryopsis (or grain), the embryo component of a dried caryopsis will imbibe water. The presence of water triggers the production of the hormone gibberellic acid in the embryo. In barley and other grass caryopsis, the embryo releases the gibberillic acid which in turn causes expression of a number of genes in the aleurone layer of the endosperm resulting in the production of a number of enzymes such as α-arnylases, proteases and β-glucanases. Similar enzymes are also produced by expression of genes in the epithelial layer.

These degradative enzymes digest certain components of the developing caryopsis (or grain) to form sugars and amino acids.

For example, the α-amylases digest the starch store in the starchy endosperm, whereas the proteases digest the storage proteins and the β-glucanases digest the cell walls. The resultant sugars and amino acids cross the epithelial layer and trigger growth of the shoot and root of the embryo axis—i.e. start the germination process.

In some cases it is desirable to transform seeds, grains, caryopsis and plants by introducing genes which, as a result of their expression, yield new or improved properties to the resulting transformed seeds, grains, caryopsis or plants. For example, it may be desirable to alter the expression levels of a natural structural gene which may be under- or over-expressed. It may even be desirable to reduce or eliminate a disease which harms or destroys the seed, grain, caryopsis or the plant.

It may even be desirable to make the seed, grain, caryopsis or the plant resistant to herbicides. It may even be desirable to prevent or to reduce the extent of pre-harvest sprouting.

It may even be desirable for the seed, grain, caryopsis, or plant to produce compounds useful for mammalian usage, such as human insulin.

Some techniques are known for addressing some of those aims.

For example, the bacterium *Agrobacterium tumefaciens* has been used to introduce desired genes into the chromosome of a plant. For example the gene coding for EPSP synthase, a key enzyme in the synthesis of aromatic acids in plants, has been isolated and introduced into petunia plants under the control of a CaMV promoter (Shah et al., [1986]). The transgenic plants expressed increased levels of EPSP synthase in their chloroplasts and were more tolerant to glycophophate—which inhibits production of EPSP synthase.

Other examples may be found in R. W. Old & S. B. Primrose (1993). Another use of *Agrobacterium tumefaciens* is described in De Silva et al. (1992) wherein a recombinant DNA construct is described containing a plant plastid specific promoter that expresses a gene placed under its control in concert with the fatty acid or lipid biosynthesis in the plant cell.

PCT WO 90/01551 mentions the use of the aleurone cells of mature, germinating caryopsis to produce proteins from GOIs under the control of an α-amylase promoter. This promoter is active only in germinating caryopsis.

Non-specific lipid transfer proteins (nsLtps) have the ability to mediate in vitro transfer of radiolabelled phospholipids from liposomal donor membranes to mitochondrial acceptor membranes (Kader et al., 1984; Watanabe and Yamada, 1986). Although their in vivo function remains unclear, nsLTPs from plants have recently received much attention due to their recurrent isolation as cDNA clones representing developmentally regulated transcripts expressed in several different tissues. A common feature is that, at some point in their development, they are highly expressed in tissues producing an extracellular layer rich in lipids.

In particular, transcripts corresponding to cDNAs encoding 10 kDa nsLTPs have been characterized in the tapetum cells of anthers as well as the epidermal layers of leaves and shoots in tobacco (Koltunow et al., 1990; Fleming et al., 1992), and barley aleurone layers (Mundy and Rogers, 1986; Jakobsen et al., 1989).

In addition, a 10 kDa nsLTP has been discovered to be one of the proteins secreted from auxin-treated somatic carrot embryos into the tissue culture medium (Sterk et al., 1991).

Based on in situ hybridisation data demonstrating that the Ltp transcripts are localized in the protoderm cells of the somatic and zygotic carrot embryo, it was suggested that in vivo nsLTPs are involved in either cutin biosynthesis or in the biogenesis and degradation of storage lipids (Sossountzov et al., 1991; Sterk et al., 1991).

A nsLTP in Arabidopsis has been localized to the cell walls lending further support to an extracellular function of this class of proteins (Thoma et al., 1993).

Recently, using a standard in vitro Ltp assay, two 10 kDa nsLtps and one member of a novel class of 7 kDa nsLtp's were isolated from wheat seeds (Monnet, 1990; Dieryck et al., 1992).

The sequence of this 7 kDa wheat nsLtp protein shows a high degree of similarity with the predicted protein from the open reading frame (ORF) of the Bz11E cDNA, which had been isolated in a differential screening for barley aleurone specific transcripts (Jakobsen et al., 1989). However, the amino acid sequence of this polypeptide showed only limited sequence identities with the previously sequenced 10 kDa proteins. In sub-cellular localisation studies using gold labelled antibodies one 10 kDa protein from Arabidopsis was localised to the cell wall of epidermal leaf cells. The presence of a signal peptide domain in the N-terminus of the open reading frames of all characterised plant nsLtp cDNAs, also suggests that these are proteins destined for the secretory pathway with a possible extracellular function.

Olsen et al. in a paper titled "Molecular Strategies For Improving Pre-Harvest Sprouting Resistance In Cereals" published in 1990 in the published extracts from the Fifth International Symposium On Pre-Harvest Sprouting In Cereals (Westview Press Inc.) describe three different strategies for expressing different "effector" genes in the aleurone layer in developing grains of transgenic plants. This document mentions 4 promoter systems—including a system called B11E.

Kalla et al. (1993) in a paper titled "Characterisation of Promoter Elements Of Aleurone Specific Genes From Barley" describe the possibility of the expression of anti-sense genes by the use of promoters of the aleurone genes B22E, B23D, B14D, and B11E.

Linnestad et al. (1991) describe the isolation and sequencing of the Ltp1 gene and disclose a 787 base pair fragment of the Ltp1 gene promoter fused to a fragment of the Ltp1 structural gene. This paper does not disclose any expression studies using the 787 base pair fragment.

Skriver et al. (1992) report further on the Ltp1 gene. This paper says that the Ltp1 gene promoter is only aleurone specific. To confirm this submission the paper further reports on the isolation and fusion of a 769 bp fragment (−702 to +67 bp) of the gene to the bacterial β-glucuronidase (GUS) reporter gene. This fragment therefore contains 635 bp of the Ltp1 gene promoter. Subsequent transient expression studies showed that the shortened gene promoter resulted only in aleurone specific expression. Expression was not observed in any other tissue. The authors conclude that there are sequences between the −702 and +67 bp of Ltp1 which contain DNA elements that specifically modulate its transcription in aleurone cells.

One of the major limitations to the molecular breeding of new types of crop plants with specific cells expressing GOIs is the lack of a suitable tissue specific promoter. In particular, there is a lack of a tissue specific promoter that leads to expression of a GOI in a developing caryopsis (or grain) or in a germinating rice seedling or in a developing grain, in particular in the scutellar epithelial tissue or vascular tissue of a germinating seedling or a developing grain or a plant.

Moreover, all of the available promoters—such as the CaMV 35S, rice actin and maize alcohol dehydrogenase—are constitutive, i.e. they are fairly non-specific in target site or stage development as they drive expression in most cell types in the plants.

Hence, another problem that arises is how to achieve expression of a product coded for by a GOI in a specific tissue that gives minimal interference with the developing embryo and seedling.

Our co-pending United Kingdom patent application (GB 9324707.0) describes the use of an Ltp2 gene promoter for expression of a GOI in the aleurone layer. However, in spite of this teaching, there is still a need for other tissue specific promoters, such as another aleurone specific promoter or, preferably, a promoter specific for vascular tissue and/or the scutellar epithelial layer. In this regard, it is still desirable to provide other tissue specific expression of GOIs in cereals such as rice, maize, wheat, barley and other transgenic cereal plants. Moreover it is desirable to provide tissue specific expression that does not detrimentally affect the developing embryo and the developing caryopsis (or grain).

According to a first aspect of the present invention there is provided a modified Ltp1 gene promoter which is integrated, preferably stably integrated, within a plant material's genomic DNA and which is capable of inducing expression of a GOI when fused to the gene promoter in at least the aleurone cells or in at least the scutellar epithelial tissue or vascular tissue of a germinating seedling or a developing grain or a plant (e.g. in the root, leaves and stem).

According to a second aspect of the present invention there is provided a modified Ltp1 gene promoter according to claim 1 or claim 2 wherein the promoter comprises the nucleic acid sequence shown as SEQ ID NO: 1, or a sequence that has substantial homology with that of SEQ. I.D. 1, or a variant thereof.

According to a third aspect of the present invention there is provided an isolated Ltp1 gene promoter comprising the sequence shown as SEQ ID NO: 1, or a sequence that has substantial homology therewith, or a variant thereof.

According to a fourth aspect of the present invention there is provided a construct comprising a GOI and a modified Ltp1 gene promoter according to the present invention; wherein the construct is capable of being expressed in at least the aleurone cells or in at least the scutellar epithelial tissue or vascular tissue of a plant material; and wherein if there is expression in just the aleurone layer of a developing barley caryopsis then the fused promoter and GOI are not the 769 bp fragment of Skriver et al (1992).

According to a fifth aspect of the present invention there is provided an expression system for at least the aleurone cells or for at least the scutellar epithelial tissue or vascular tissue of a plant material, the expression system comprising a GOI fused to a modified Ltp1 gene promoter wherein the expression system is capable of being expressed in at least the aleurone cells or in at least the scutellar epithelial tissue or vascular tissue of the plant material; and wherein if there is expression in just the aleurone layer of a developing barley caryopsis then the fused promoter and GOI are not the 769 bp fragment of Skriver et al (1992).

According to a sixth aspect of the present invention there is provided an expression system for at least the aleurone cells of a developing caryopsis or for at least the scutellar epithelial tissue or vascular tissue of a germinating seedling or developing grain or plant (e.g. in the root, leaves and stem), the expression system comprising a gene promoter fused to a GOI wherein the expression system is capable of being expressed in at least the aleurone cells of the developing caryopsis or in at least the scutellar epithelial tissue or vascular tissue of a germinating seedling or a developing grain or a plant (e.g. in the root, leaves and stem); either wherein if there is expression in just the aleurone layer of a developing barley caryopsis then either the promoter is not the wild type Ltp1 promoter in its natural enviroment and the GOI is not the Ltp1 functional gene in its natural enviroment; or wherein if there is expression in just the aleurone layer of a developing caryopsis then the fused promoter and GOI are not the 769 bp fragment of Skriver et al (1992).

According to a seventh aspect of the present invention there is provided a transgenic cereal comprising an expression system according to the present invention or a construct according to the present invention wherein the expression system or construct is integrated, preferably stably integrated, within the cereal's genomic DNA.

According to an eighth aspect of the present invention there is provided the use of a gene promoter according to the present invention to induce expression of a GOI when fused to the gene promoter in at least the aleurone cells or in at least the scutellar epithelial tissue or vascular tissue of a plant material.

According to a ninth aspect of the present invention there is provided a process of expressing a GOI when fused to a gene promoter according to the present invention wherein expression occurs in at least the aleurone cells or in at least the scutellar epithelial tissue or vascular tissue of a plant material.

According to a tenth aspect of the present invention there is provided a process of expressing in at least the scutellar epithelial tissue or vascular tissue of a developing grain or a germinating seedling or a plant, preferably a developing rice grain or a germinating rice seedling or a transgenic rice plant, an expression system according to the present invention or a construct according to the present invention wherein the expression system or construct is integrated, preferably stably integrated, within the cereal's genomic DNA.

According to an eleventh aspect of the present invention there is provided a combination expression system comprising a. as a first construct, a construct according to the present invention; and b. as a second construct, a construct comprising a GOI and another gene promoter that is tissue- or stage-specific.

According to a twelfth aspect of the present invention there is provided a developing cereal grain, preferably a germinating rice seedling, comprising any one of: a promoter according to the present invention, an expression system according to the present invention, a construct according to the present invention, or a combination expression system according to the present invention.

According to a thirteenth aspect of the present invention there is provided plasmid NCIMB 40609.

Preferably the plant material is a developing caryopsis, a germinating seedling, a developing grain or a plant.

Preferably the construct is capable of being expressed in at least the aleurone cells of a developing caryopsis or in at least the scutellar epithelial tissue or vascular tissue of a germinating seedling or a developing grain or a plant when the construct is integrated, preferably stably integrated, within the caryopsis's or grain's or seedling's or plant's genomic DNA.

Preferably the modified Ltp1 gene promoter comprises the nucleic acid sequence shown as SEQ ID NO: 1, or a sequence that has substantial homology with that of SEQ ID NO: 1, or a variant thereof.

Preferably the construct further comprises at least one additional sequence to increase expression of the GOI.

Preferably the expression system is for at least the aleurone cells of a developing caryopsis or for at least the scutellar epithelial tissue or vascular tissue of a germinating seedling or developing grain or plant (e.g. in the root, leaves and stem).

Preferably the expression system is additionally capable of being expressed in the embryo cells of the germinating grain or the plantlet.

Preferably the expression system is integrated, preferably stably integrated, within a developing caryopsis's genomic DNA or a germinating seedling's genomic DNA or a developing grain's genomic DNA or a plant's genomic DNA.

Preferably, in the expression system, the gene promoter comprises the sequence shown as SEQ ID NO: 1 or comprises a sequence that has substantial homology therewith, or is a variant thereof.

Preferably, the expression system comprises the construct according to the present invention.

Preferably, in the use, the gene promoter is used to induce expression of a GOI when fused to the gene promoter in at least the aleurone cells of a developing caryopsis or in at least the scutellar epithelial tissue or vascular tissue of a germinating seedling or a developing grain or a plant (e.g. in the root, leaves and stem).

Preferably, the gene promoter expresses the GOI when fused to the gene promoter in at least the aleurone cells of a developing caryopsis or in at least the scutellar epithelial tissue or vascular tissue of a germinating seedling or a developing grain or a plant (e.g. in the root, leaves and stem).

Preferably the promoter and GOI are integrated, preferably stably integrated, within a cereal's genomic DNA.

Preferably the gene promoter is a fragment of a barley Ltp1 gene promoter.

Preferably the promoter is for a 10 kDa lipid transfer protein.

Preferably the gene promoter is obtainable from plasmid NCIMB 40609.

Preferably the gene promoter is used for expression of a GOI in a cereal caryopsis or a cereal grain or a cereal seedling or a cereal plant.

Preferably the cereal caryopsis is a developing cereal caryopsis, the cereal grain is a developing cereal grain, and the cereal seedling is a germinating cereal seedling.

Preferably the cereal is any one of a rice, maize, wheat, or barley.

Preferably the cereal is rice or maize.

Preferably the developing caryopsis is a developing barley caryopsis, the germinating seedling is a germinating rice seedling, the developing grain is a developing rice grain, and the plant is a transgenic rice plant.

Preferably in the combination expression system each construct is integrated, preferably stably integrated, within a plant material.

Preferably each of the myb site and the myc site in the gene promoter is maintained substantially intact.

Preferably the gene promoter is integrated, preferably stably integrated, in the developing caryopsis's genomic DNA or the germinating seedling's genomic DNA or the developing grain's genomic DNA or the plant's genomic DNA and which is capable of inducing expression of a GOI when fused to the gene promoter in at least the aleurone cells of the developing caryopsis or in at least the scutellar epithelial tissue or vascular tissue of a germinating seedling or a developing grain or a plant (e.g. in the root, leaves and stem).

Preferably the transgenic developing caryopsis, germinating seedling, developing grain or plant is prepared by stable integration of the GOI and the gene promoter to form a stable transgenic plant. This ensures aleurone or epithelial or vascular expression at, at least, the developing caryopsis stage. One preferred method for achieving this includes preparing the transgenic developing caryospis, germinating seedling, developing grain or plant by stable integration of the GOI and the gene promoter at the protoplast level.

Preferably the promoter is used for expression of a GOI in a monocotyledonous species, including a grass— preferably a transgenic cereal grain or caryopsis. Preferably the gene promoter is used for expression of a GOI in a cereal grain or caryopsis. Preferably the cereal grain or caryopsis is a developing cereal grain or caryopsis. Preferably the cereal grain or caryopsis is any one of a rice, maize, wheat, or barley grain or caryopsis.

Preferably the cereal grain is a rice grain.

Preferably the DNA sequence for the modified Ltp1 gene promoter is the nucleic acid sequence shown as SEQ ID NO: 1.

Preferably in the combination expression system each construct is integrated, preferably stably integrated, within a developing caryopsis's genomic DNA or a grain's genomic DNA or a seedling's genomic DNA or a plant's genomic DNA.

Preferably, in the combination expression system, the first construct comprises the modified Ltp1 gene promoter according to the present invention.

Preferably, the promoter in the second construct is an aleurone specific promoter.

Preferably the promoter in the second construct a barley promoter.

Preferably the second construct is the B22E gene promoter.

Preferably the promoter in the second construct is the Ltp2 gene promoter.

Preferably the promoter in the second construct is for a 7 kDa lipid transfer protein.

Preferably the promoter in the second construct is the promoter for Ltp2 of *Hordeum vulgare*.

Preferably the promoter in the second construct comprises the sequence shown as SEQ ID NO: 2, or a sequence that has substantial homology therewith, or a variant thereof.

Preferably each of the myb site and the myc site in the Ltp2 gene promoter is maintained substantially intact.

Preferably the second construct further comprises at least one additional sequence to increase expression of the GOI.

Preferably, in the combination expression system, the grain or caryopsis is as defined above for the present invention.

Preferably the gene promoter is obtainable from plasmid NCIMB 40609.

A preferred embodiment of the present invention is a modified Ltp1 gene promoter which is integrated, preferably stably integrated, within a plant material's genomic DNA and which is capable of inducing expression of a GOI when fused to the gene promoter in at least the aleurone cells or in at least the scutellar epithelial tissue or vascular tissue of a germinating seedling or a developing grain or a plant (e.g. in the root, leaves and stem), but wherein if there is expression in just the aleurone layer of a developing seed then the fused promoter and GOI are not the 769 bp fragment of Skriver et al (1992).

An even more preferred embodiment of the present invention is a modified Ltp1 gene promoter which is integrated, preferably stably integrated, within a plant material's genomic DNA and which is capable of inducing expression of a GOI when fused to the gene promoter in at least the aleurone cells or in at least the scutellar epithelial tissue or vascular tissue of a germinating seedling or a developing grain or a plant (e.g. in the root, leaves and stem), wherein the promoter comprises the nucleic acid sequence shown as SEQ ID NO: 1, or a sequence that has substantial homology with that of SEQ ID NO: 1, or a variant thereof.

As a highly preferred embodiment, the present invention therefore provides transgenic rice comprising a construct comprising a GOI fused to a modified Ltp1 gene promoter; wherein the construct is integrated, preferably stably integrated, within the rice's genomic DNA, and wherein the GOI is expressed in at least the vascular tissue and/or scutellar epithelial layer of a germinating rice seedling or a developing rice grain or a rice plant.

In a more preferred embodiment the present invention provides a transgenic rice seedling, grain or plant comprising a construct comprising a GOI fused to a modified Ltp1 gene promoter, wherein the construct is integrated, preferably stably integrated, within the rice's genomic DNA; wherein the GOI is expressed in at least the scutellar epithelial tissue or vascular tissue of a germinating seedling or a developing grain or a plant, and wherein the modified Ltp1 gene promoter comprises the nucleic acid sequence shown as SEQ ID NO: 1, or a sequence that has substantial homology with that of SEQ ID NO: 1, or a variant thereof.

The additional sequence(s) for the construct(s) for increasing the expression of the GOI(s) may be one or more repeats (e.g. tandem repeats) of the promoter upstream box(es) which are responsible for the aleurone layer or scutellar epithelial cell and/or vascular expression pattern of the modified Ltp1 gene promoter. The additional sequence may even be a Sh1-intron.

The term "plant material" includes a developing caryopsis, a germinating caryopsis or grain, or a seedling, a plantlet or a plant, or tissues or cells thereof, such as the aleurone cells of a developing caryopsis or the scutellar epithelial tissue or vascular tissue of a germinating seedling or developing grain or plant (e.g. in the root, leaves and stem).

Thus a preferred aspect of the present invention comprises plant material comprising a GOI and a modified Ltp1 gene promoter which is capable of inducing expression of the GOI when fused to the gene promoter in at least the aleurone cells or in at least the scutellar epithelial tissue or vascular tissue of the plant material; wherein the construct is capable of being expressed in at least the aleurone cells or in at least the scutellar epithelial tissue or vascular tissue of the plant material, when the construct is integrated, preferably stably integrated, within the caryopsis's or grain's or seedling's or plant's genomic DNA; and wherein the modified Ltp1 gene promoter comprises the nucleic acid sequence shown as SEQ ID NO: 1, or a sequence that has substantial homology with that of SEQ ID NO: 1, or a variant thereof.

The term "modified" with reference to the present invention means any Ltp1 gene promoter that is different to the wild type promoter but wherein the promoter induces expression in at least the aleurone cells of a developing caryopsis or in at least the scutellar epithelial tissue or vascular tissue of a germinating seedling or a developing grain or a plant (e.g. in the root, leaves and stem).

In particular, a preferred modified Ltp1 gene promoter is a shortened wild type Ltp1 gene promoter but wherein the promoter induces expression in at least the aleurone cells of a developing caryopsis or in at least the scutellar epithelial tissue or vascular tissue of a germinating seedling or a developing grain or a plant (e.g. in the root, leaves and stem).

The term "transgenic" in relation to the present invention—in particular in relation to the developing caryopsis, germinating seedlings, developing grains and plants of the present invention—does not include a wild type promoter in its natural enviroment in combination with its associated functional gene (GOI) in its natural enviroment. Thus, the term includes developing caryopsis or seedlings or grains or plants incorporating the GOI which may be natural or non-natural to the grain or caryopsis or seedling or grain or plant in question operatively linked to the modified Ltp1 promoter of the present invention.

The term "GOI" with reference to the present invention means any gene of interest. A GOI can be any gene that is either foreign or natural to the cereal in question, except for the wild type Ltp1 functional gene when in its natural enviroment. In the combination expression system the GOI may be the same or different.

Typical examples of a GOI include genes encoding for proteins and enzymes that modify metabolic and catabolic processes. For example, the GOI may be a protein giving added nutritional value to the grain or caryopsis as a food or crop. Typical examples include plant proteins that can inhibit the formation of anti-nutritive factors and plant proteins that have a more desirable amino acid composition (e.g. a higher lysine content than the non-transgenic plant).

The GOI may even code for an enzyme that can be used in food processing such as chymosin, thaumatin, α-galactosidase and guar.

In a preferred embodiment, particularly with vascular expression, the GOI may code for an agent for introducing or increasing pathogen resistance.

The GOI may even be an antisense construct for modifying the expression of natural transcripts present in the relevant tissues.

The GOI may even code for a non-natural plant compound that is of benefit to animals or humans. For example, the GOI could code for a pharmaceutically active protein or enzyme such as the therapeutic compounds insulin, interferon, human serum albumin, human growth factor and blood clotting factors. In this regard, the transformed cereal grain or caryopsis could prepare acceptable quantities of the desired compound which could be easily retrievable from the scutellar epithelial layer, the aleurone layer or the vascular tissue.

Preferably the GOI is a gene encoding for any one of a protein having a high nutritional value, a *Bacillus thuringensis* insect toxin, an α- or β- amylase antisense transcript, a protease antisense transcript, or a glucanase antisense transcript.

The term "a variant thereof" with reference to the present invention means any substitution of, variation of, modification of, replacement of, deletion of or the addition of one or more nucleic acid(s) from or to the promoter sequence providing the resultant sequence exhibits at least aleurone, scutellar epithelial or vascular expression, respectively. The term also includes sequences that can substantially hybridise to the promoter sequence.

The term "substantial homology" covers homology with respect to at least the essential nucleic acids/nucleic acid residues of the promoter sequence providing the homologous sequence acts as a promoter, e.g. as a promoter for at least aleurone expression in a developing caryopsis or for at least scutellar epithelial tissue or vascular tissue expression in a germinating seedling or in a developing grain or plant. Preferably there is at least about 80% homology, more preferably at least about 90% homology, and even more preferably there is at least about 95% homology with the promoter sequence shown as SEQ ID NO: 1. or SEQ ID NO: 2, respectively.

The term "maintained substantially intact" means that at least the essential components of each of the myb site and the myc site remain in the construct to ensure acceptable expression of a GOI. Preferably at least about 75%, more preferably at least about 90%, and even more preferably there is at least about 95%, of the myb or myc site is left intact.

The term "construct"—which is synonymous with terms such as "cassette", "hybrid" and "conjugate"—includes a GOI directly or indirectly attached to the modified gene promoter, such as to form a [modified Ltp1 gene promoter-GOI] cassette. An example of an indirect attachment is the provision of a suitable spacer group such as an intron sequence, such as the Sh1-intron, intermediate the promoter and the GOI. The same is true for the term "fused" in relation to the present invention which includes direct or indirect attachment.

The term "expression system" means that the system defined above can be expressed in an appropriate organism, tissue, cell or medium. In this regard, the expression system of the present invention may comprise additional components that ensure ro increase the expression of the GOI by use of the gene promoter.

As indicated above, the expression system of the present invention can also be used in conjunction with another expression system, preferably an expression system that is also tissue and/or stage specific.

For example, the construct comprising the modified Ltp1 gene promoter (e.g. the 787 bp fragment of SEQ ID NO: 1) can be used in conjunction with a construct comprising the Ltp2 gene promoter (e.g. SEQ ID NO: NO. 2)—which is the subject of our co-pending UK patent application GB 9324707.0.

In this respect, and with reference to barley, in the early stages of developing caryopsis the modified Ltp1 gene promoter affects expression of a GOI in at least the aleurone layers of developing caryopsis. This expression can then be complimented by use of the Ltp2 gene which can express a GOI (which may be the same or different as that operatively linked to the modified Ltp1 gene promoter) in high levels in the aleurone layer of developing grains.

However, the combination expression system is very effective for transgenic rice. In this respect, in the early stages of developing caryopsis the modified Ltp1 gene promoter expresses a GOI in the scutellar epithelial layer and the vascular tissue. This expression can then be complimented by use of the Ltp2 gene which can express a GOI in high levels in the aleurone layer of developing grains. This combination is particularly advantageous for pre-harvest sprouting when the first response is production of α-amylase in the scutellar epithelium cells as this can be reduced or prevented by placing an anti-sense α amylase gene under the control of the Ltp1 promoter. In this system, the expression of antisense α-amylase would block the synthesis of α-amylases in the scutellum epithelial cells—where they are first made. The same or another GOI could be expressed in the aleurone layer via the Ltp2 gene promoter.

The construct comprising the modified Ltp1 gene promoter may even be used in conjunction with a construct comprising the B22E gene promoter—details of which may be found in Olsen et al. (1990) and Klemsdal et al., (1991). This gene promoter, which is expressed in immature aleurone layers, has been shown by particle bombardment experiments to be capable of driving Gus expression in developing barley grains. Also, using Northern analysis, as well as in situ hybridization, it has been shown that the B22E cDNA probe hybridizes to transcripts in the aleurone layer and in the scutellum parenchyma cells and the provascular bundle of the embryo axis in developing barley grains. In addition, a hybridizing transcript is also present in the ventral vascular strand of developing caryopsis (Olsen et al., 1990).

We have also found that by using a 4.6 kb B22E promoter fragment contained on a XbaI-ClaI fragment of a genomic clone fused to the Gus reporter gene transformed rice plants could be prepared. Those transformed rice plants exhibited strong expression in the vascular tissue (phloem) of the ventral strand of the developing rice grain. This expression pattern was completely unexpected in view of Klemsdal et al (1991). Expression, although weaker, in the same cell type was also observable in the stem of young shoots. Thus, using the B22E promoter, a GOI transcript can be expressed in the aleurone layers of developing grains, the parenchyma cells of the embryonic scutellum and the ventral vascular bundle of developing grains.

The combination of the use of the modified Ltp1 gene promoter and the B22E gene promoter could even include the use of another gene promoter, such as the Ltp2 gene promoter, to express three GOIs respectively wherein each GOI may be the same or different.

One or more of the other expression systems to be used in conjunction with the modified Ltp1 gene promoter expression system may be contained in or on the same transmission vector—such as in the same transforming baterium or even in the same plasmid. The advantage of this is that each expression system can then be delivered at the same time. The respective expression systems will then be turned on during the relevant life time of the grain or caryopsis or the plantlet or the mature plant.

The present invention therefore provides the novel and inventive use of a promoter which can express a GOI in at least the aleurone cells of a developing caryopsis or in at least the scutellar epithelial tissue or vascular tissue of a germinating seedling or a developing grain or a plant (e.g. in the root, leaves and stem). In a preferred embodiment the present invention relates to the use of a modified Ltp1 gene promoter, preferably the Ltp1 gene promoter is obtainable from barley.

The main advantage of the present invention is that the use of the modified Ltp1 gene promoter results in expression of a GOI in at least the aleurone layer of at least a developing caryopsis, such as a developing barley caryopsis, or in at least the scutellar epithelial tissue or vascular tissue of a germinating seedling or a developing grain or plant of cereals such as rice, maize, wheat or other transgenic cereal grain or caryopsis, preferably a developing rice grain.

Another advantage is that, depending on the type of GOI, the expressed products can be stable in vivo. Hence over a period of time high levels of the expressed product can accumulate in the aleurone cells or in epithelial cells or in the vascular tissue.

A further advantage is that the expression of the product coded for by a GOI in the aleurone layer or the epithelial layer or the vascular tissue has minimal interference with the developing embryo and seedling. This is in direct contrast to known constitutive promoters which give high levels of expression in the developing seedling and mature plant tissues which severely affect normal plant development. Thus the present invention is particularly useful for expressing a GOI in at least the aleurone layer of a developing caryopsis or in at least the scutellar epithelial tissue or in the scutellar epithelial tissue or vascular tissue of a germinating seedling or a developing grain or plant—such as cereal grains or caryopsis—and in doing so not detrimentaly affect the caryopsis, seedling, grain or plant.

With regard to the first aspect of the present invention it is to be noted that this is the first reported case for the specific expression of a GOI in the scutellar epithelial cells or vascular cells of a transformed developing cereal grain such as rice.

With regard to some aspects of the present invention, it is to be noted that up until now it was believed that the wild type Ltp1 gene promoter or a specific variant thereof when fused to at least a segment of the Ltp1 functional gene would lead only to expression in the aleurone layer. For example see the teachings of Skriver et al. (1992). However, with the present invention, we have now surprisingly found that this is not the case and it is now possible to modify the Ltp1 gene promoter to lead to a pronounced expression in at least the aleurone layer or in at least the scutellar epithelial layer or vascular tissue of a plant material.

In one embodiment the plant material is barley plant material. In another embodiment the plant material is not barley plant material. In a preferred embodiment the plant material is rice plant material. In an alternative preferred embodiment the plant material is maize plant material.

In a germinating, transgenic barley caryopsis according to the present invention, there is expression in the aleurone layer.

In a germinating, transgenic rice seedling according to the present invention there is pronounced expression in the scutellar epithelial tissue and vascular tissue.

As indicated, the expression pattern for the present invention is particularly surprising as it was completely unexpected that a modified Ltp1 gene promoter could result in expression of a GOI, such as a plant functional gene, in the aleurone cells of, for example, barley or in the scutellar epithelial tissue or vascular tissue of a germinating seedling or a developing grain or plant of rice (see experimental section later). The findings of the present invention are also surprisingly different to the work of Skriver et al. (1992) who, as mentioned above, report that the Ltp1 gene promoter and a shortened version thereof when fused to the functional Ltp1 functional gene only result in aleurone specific expression in barley—i.e. expression is not observed in any other tissue in barley or even other cereals.

In order to prepare the transgenic organism according to the present invention, the modified Ltp1 gene promoter may be initially inserted into a plasmid. For example, the SacI-BclI Ltp1 gene promoter fragment can be inserted into the SacI-BamHI site of Bluescript. A GOI, such as GUS, can then be inserted into this construct. Furthermore, a Sh1 intron can then be inserted into the SmaI site of this construct.

Stable integration into protoplasts may be achieved by using the method of Shimamoto (1989). Another way is by bombardment of an embryonic suspension of cells (e.g. rice, barley or maize cells). A further way is by bombardment of immature embryos (e.g. rice, maize or barley embryos).

With regard to the present invention, it is shown by using particle bombardments that the modified Ltp1 gene promoter, such as the 787 bp fragment of the attached sequence, when fused to a β-glucuronidase (GUS) reporter gene, which serves as a GOI for the purposes of this invention, acts as a promoter for expression of GUS in a specific tissue type or specific tissue types. For example, GUS expression can be achieved in the aleurone cells of developing cereal caryopsis or grain, in particular developing barley caryopsis, or in the scutellar epithelial tissue or vascular tissue of a germinating seedling or a developing grain or plant, in particular developing rice grain or germinating seedlings.

In particular, in transgenic rice plants, the modified barley Ltp1 gene promoter directs strong expression of the GUS-reporter gene in the scutellar epithelial layer and the vascular tissue of the developing caryopsis. This expression can continue through into the germinating grains. The surprising finding is that very pronounced expression can be seen in the scutellar epithelial tissue or vascular tissue of a developing rice grain or germinating rice seedlings. Other examples include expression in the vascular bundles and tip of emerging shoots and roots, leaf veins and vascular bundles of stems.

Generally therefore the present invention relates to a modified promoter for a Ltp1 gene encoding a 10 kDa nsLTP. In the present invention, a genomic clone was isolated using the cDNA insert of previously isolated cDNA clone and characterised by DNA sequencing (see discussion later). The sequence of the cDNA and isolated genomic clone was found to be identical in the overlapping region. It was found the Ltp1 gene contains one intron (see discussion later).

By comparing the DNA sequence of the active promoter sequences two putative cis-acting elements with the potential of binding known transcriptional factors present in cereals were detected. They include the binding sites for transcriptional factors of the myb and myc class, namely TAACTG and CANNTG respectively. Our studies showed that high levels of expression are achieved when the myb and myc sites are left intact.

In the present invention, mature fertile rice plants were regenerated from transformed cultured rice protoplasts. The developing caryopsis of these primary transfornants were analyzed for the expression of GUS. It was found that the modified barley Ltp1 gene promoter confers some expression in the aleurone layer of the transgenic rice plants. However, pronounced expression was observed in the scutellar epithelial tissue or vascular tissue of germinating rice seedlings or developing transgenic rice grain or transgenic rice plants. This is the first example of such patterns of expression in transgenic rice plants.

The following sample has been deposited in accordance with the Budapest Treaty at the recognized depository The National Collections of Industrial and Marine Bacteria Limited (NCIMB) at 23 St. Machar Drive, Aberdeen, Scotland, AB2 1RY, United Kingdom, on Jan. 11, 1994:

An *E. Coli* K12 bacterial stock containing the plasmid pLtp1.787-GN—i.e. Bluescript containing a 787 bp fragment of the barley Ltp1 gene promoter (Deposit Number NCIMB 40609).

The plasmid pLtp1.787-GN is shown pictorially in FIG. 6 (see later).

The modified Ltp1 gene promoter can be isolated from this plasmid through the use of appropriate PCR primers, which may be easily constructed from the data from the shown sequences.

Other embodiments and aspects of the present invention include:

A transformed host having the capability of expressing a GOI in the aleurone layer or the scutellar epithelial layer or the vascular tissue through the use of the gene promoter as hereinbefore described;

A vector incorporating a construct as hereinbefore described or any part thereof;

A plasmid comprising a construct as hereinbefore described or any part thereof;

A cellular organism or cell line transformed with such a vector;

A monocotylenedonous plant comprising any one of the same;

A developing caryopsis or grain or germinating seedling comprising any of the same; and A method of expressing any one of the above.

The present invention will now be described only by way of examples in which reference shall be made to the accompanying Figures in which:

BRIEF DESCRIPTION OF THE DRAWINGS

The file of this patent application contains at least one drawing executed in color. Copies of this patent with color drawings will be provided by the Patent and Trademark Office upon request and payment of the necessary fee.

FIG. 3 is a nucleotide sequence of part of the wild type Ltp1 gene taken from Linnestad et al. (1991), Sequence ID NO: 3 and 4;

FIG. 4 is a nucleotide sequence of part of the wild type Ltp1 gene taken from Skriver et al. (1992), Sequence ID NO: 5 and 6;

FIG. 5 is a nucleotide sequence of a 787 bp fragment of the wild type Ltp1 gene promoter (SEQ ID NO: 1);

A. METHODS i. Plant material

Caryopsis of barley (*Hordeum vulgare* cv. Bomi) were collected from plants grown in a phytotron as described before (Kvaale and Olsen, 1986). The plants were emasculated and pollinated by hand and isolated in order to ensure accurate determination of caryopsis age.

ii. cDNA and genomic clones

The isolation and sequencing of the Ltp1 cDNA clone was conducted as described by Jakobsen et al. (1989). A barley, cv. Bomi genomic library was constructed by partial MboI digestion of total genomic DNA and subsequent ligation of the 10–20 kilo basepair (kb) size fraction with BamHI digested lambda EMBL3 DNA (Clontech Labs, Palo Alto, Calif., USA). Using the Ltp1 cDNA insert as a template for probe synthesis with a random labelling kit (Boehringer-Mannheim), one positive clone was identified after repeated rounds of plaque hybridization. DNA purified from this clone was restricted with several enzymes and characterized by Southern blot analysis. The sequence data obtained after this procedure are shown in FIG. 3.

iii. In situ hybridization

For in vitro transcription of antisense RNA, the plasmid Ltp1 was linearized and transcribed using MAXIscript (Ambion) and [$\alpha^{33}$P]-UTP (Amersham International). The probe was hydrolysed to fragments of about 100 bp as described by Somssich et al. (1988). Caryopsis tissues were fixed in 1% glutaraldehyde, 100 mM sodium phosphate (pH 7.0) for 2 hours and embedded in Histowax (Histolab, Göteborg, Sweden).

Barley caryopsis sections of 10 μm were pre-treated with pronase (Calbiochem) as described by (Schmelzer et al., 1988) and hybridized with 25 ml of hybridization mix (200 ng probe ml-1, 50% formamide, 10% (w/v) dextran sulphate, 0.3 M NaCl, 10 mM Tris-HCl, 1 mM EDTA (pH 7), 0.02% polyvinyl-pyrrolidone, 0.2% Ficoll, 0.02% bovine serum albumin) for 15 hours at 50° C.

Post-hybridization was carried out according to Somssich et al. (1988) and auto-radiography was done as described by Schmelzer et al. (1988).

iv. Constructs for transient expression analysis

Figure 7:
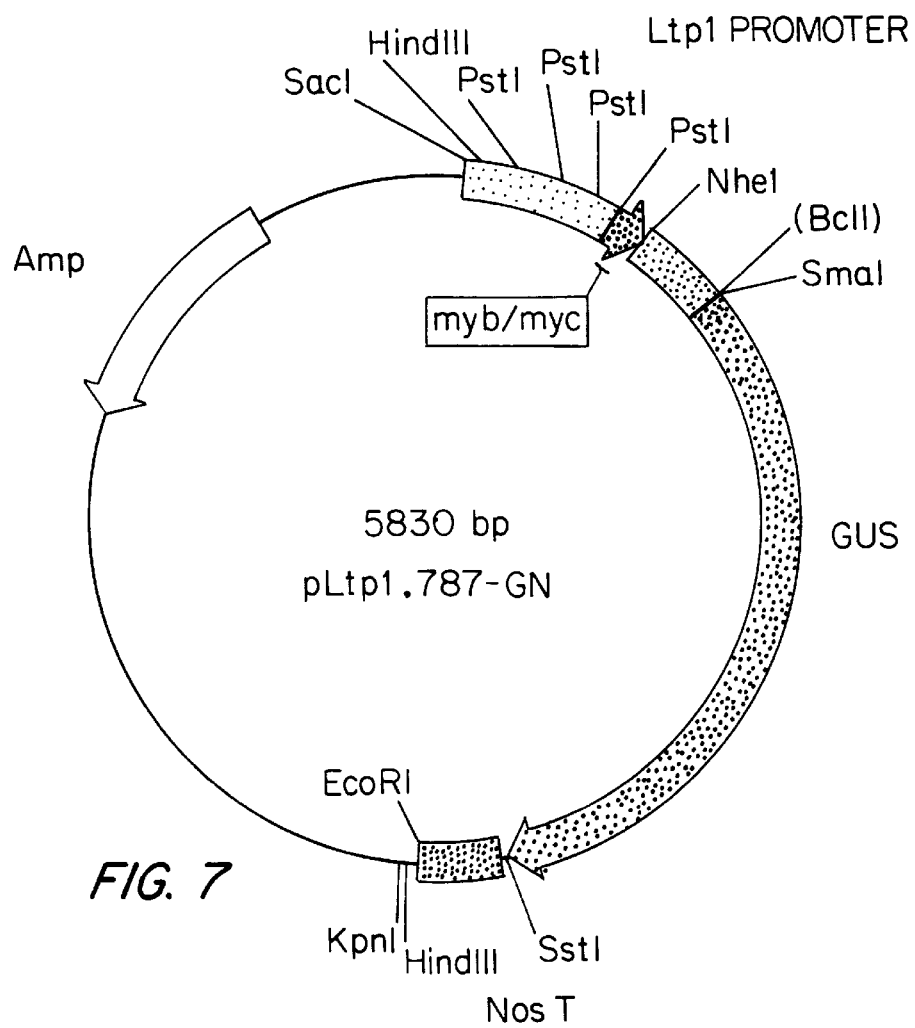
FIG. 7 is a circular map of the plasmid pLtp1.787-GN containing the Ltp1.787-GN construct.

For the micro-projectile bombardment experiments, the following was used:

pLtp1.787-GN (see FIG. 7 and associated commentary). Isolated plasmid DNA was used in the bombardment studies.

For transient assay studies with rice protoplasts, the following were studied:

pLtp1.787-GN (see FIG. 7 and associated commentary).
pLtp1.787(-myb/myc)-GN (see commentary below).

Deletion studies were performed on the modified Ltp1 gene promoter (Ltp1.787) wherein a section of DNA containing the myb and myc sites (see FIG. 3 and associated commentary) was removed to form pLtp1.787(-myb/myc)-GN. In this embodiment, the modified Ltp1 gene promoter having deletions from and between the myb and myc sites was prepared and fused to GN. In order to prepare this deleted modified Ltp1 gene promoter a PCR strategy using primers covering the flanking sequences of the deleted sequence was adopted.

v. Transformation of barley cells by particle bombardment

Barley caryopsis were harvested at 25 DAP (days after pollination), surface sterilized in 1% sodium hypochlorite for 5 min and then washed 4 times in sterile distilled water. The maternal tissues were removed to expose the aleurone layer and the caryopsis was then divided into two, longitudinally along the crease. The pieces of tissue were then placed, endosperm down, onto MS media (Murashige & Skoog 1962) with 10 g/l sucrose solidified with 10 g/l agar in plastic petri dishes (in two rows of 4 endosperm halves per dish). Embryos from the same caryopsis were placed in the same petri dishes with the scutellum side facing upwards.

Single bombardments were performed in a DuPont PDS 1000 device, with M-17 tungsten pellets (approx. 1 μm in diameter) coated with DNA as described by Gordon-Kamm et al. (1990) and using a 100 mm mesh 2 cm below the stopping plate. Histochemical staining for GUS expression was performed with X-Gluc (5-bromo,4-chloro,3-indolyl,β-D,Glucuronic acid) as described by Jefferson (1987) at 37° C. for 2 days.

In these studies, after bombardment with the pLtp1.787-GN and staining for GUS-activity, blue spots appeared both in the aleurone layer as well as in the scutellar epithelium layer. These results demonstrate that the 787 bp fragment of the Ltp1 gene promoter of the present invention is capable of driving transcription in the epithelial cells.

vi. Rice transformation

In these studies, the gene was transformed into rice by electroporation of embryogenetic protoplasts following the teachings of Shimamoto et al. 1989. Six fertile transgenic rice plants were obtained. Histochemical GUS analysis was also carried out with developing rice grains of 25 DAP and 1 to 5 day old seedings and up to 1 month old plants derived from transgenic grains. The results demonstrated expression of the Ltp1—GUS gene in the scutellar epithelial layer of developing transgenic rice plants. In addition, in a germinating rice seedling according to the present invention there is a pronounced expression in the vascular tissue.

B. RESULTS AND DISCUSSION WITH REFERENCE TO THE FIGURES

Figure 1:
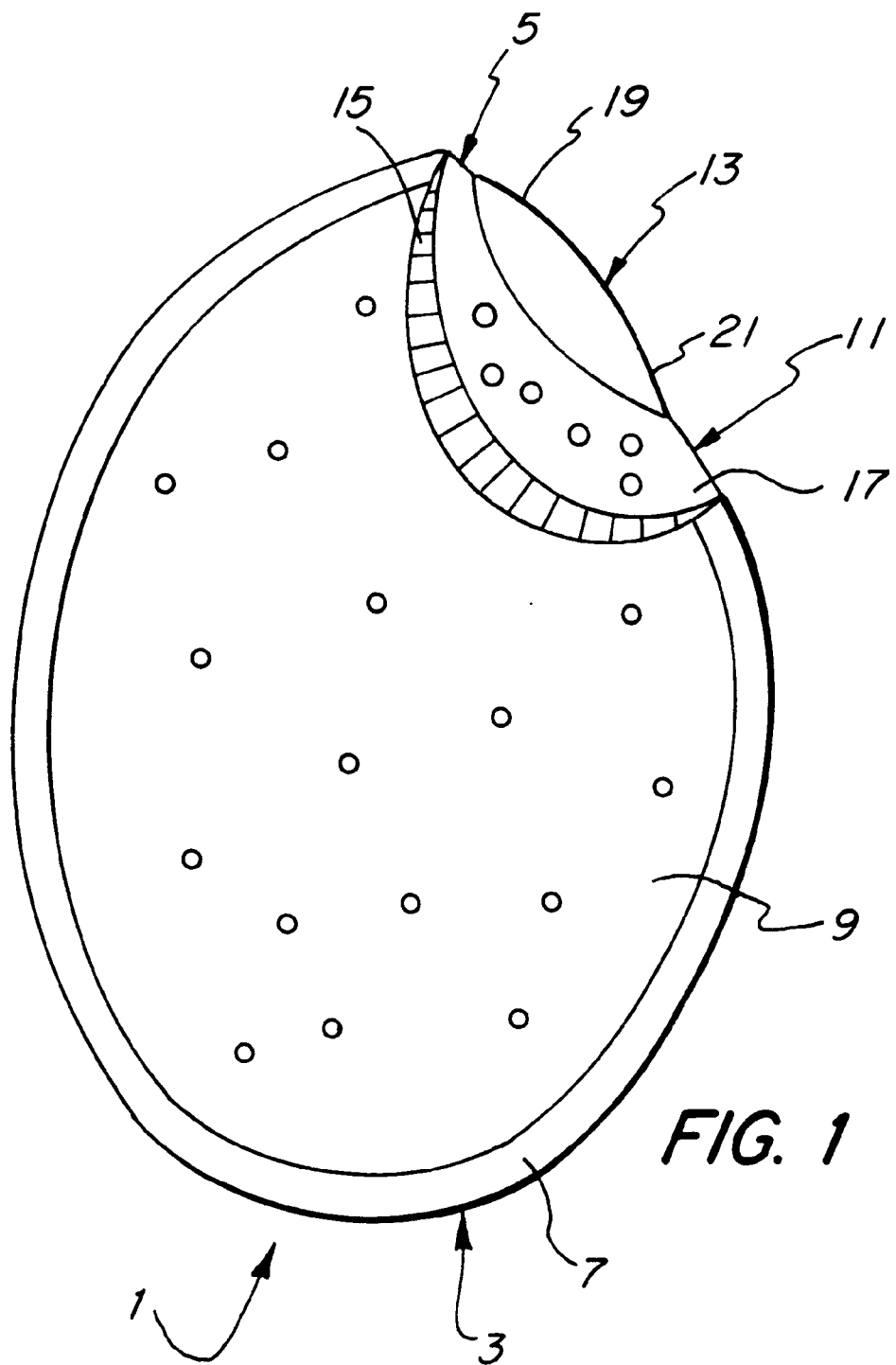
FIG. 1 is a diagrammatic illustration of the structural components of a developing caryopsis.

1. In order to explain more fully the results, reference is made to FIG. 1 which shows the major components of a typical developing caryopsis (or grain) 1. In this regard, the caryopsis (or grain) 1 comprises an endosperm component 3 and an embryo component 5. The endosperm component 3 is divisible into an outer aleurone layer 7, which is three cells thick for barley caryopsis, and a starchy endosperm 9. The embryo component 5 is divisible into a scutellum 11 and an embryo axis 13. The scutellum 11 is further divisible into an epithelial layer 15 and parenchyma layer 17. Likewise, the embryo axis 13 is further divisible into a root component 19 and a shoot component 21.

Figure 2:
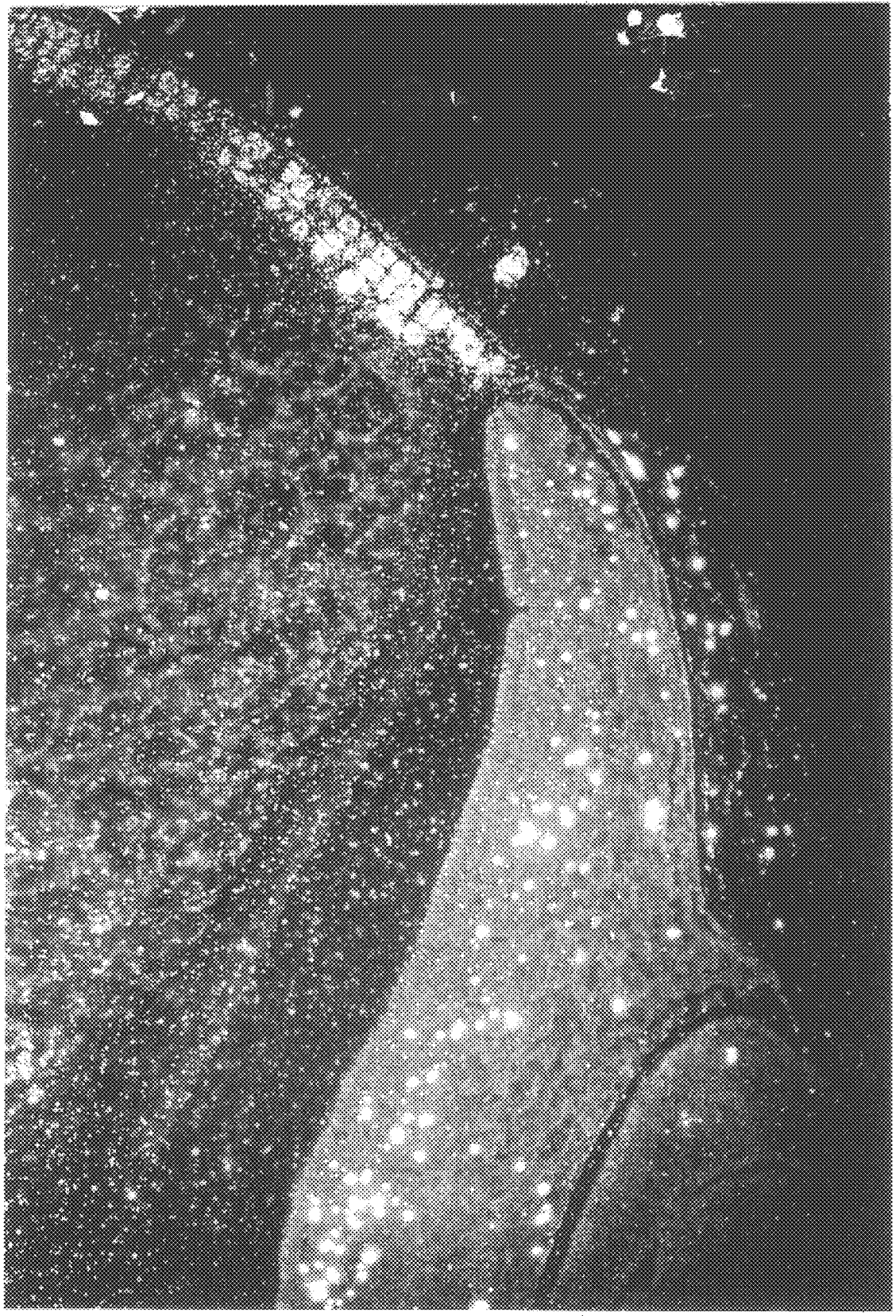
FIG. 2 shows the results for an in situ hybridization experiment for a wild type Ltp1 gene promoter in barley.

2. FIG. 2 is a transverse section of a 30 day-old wild-type developing barley caryopsis showing in situ hybridisation with a radio-labelled Ltp1 probe. The bound probe is only seen in the aleurone layer. It is not seen in any other tissue type, in particular the scutellar epithelial layer. This work confirms the work of Skriver et al. (1992).

The bright spots are due to optical interference.

3. FIG. 3 shows the nucleotide sequence and the deduced amino acid sequence of Ltp1. The intron is indicated by lower case letters. The TGA stop codon is indicated by an asterisk, the putative CAAT and TATA sequences are indicated by boxes. A 21 bp inverted repeat is indicated by arrows. Four 8 bp palindromic sequences are overlined. The motif indicated by thick underlining resembles the CATGTAAA motif present in the promoters of several genes expressed in aleurone cells (Klemsdal et al. (1991)). An AT block followed by a myb consensus recognition site and a myc binding motif are indicated by double underlining.

4. FIG. 4 shows the sequence of the Ltp1 gene. The 351 bp open reading frame is interrupted by a 133 bp intron (+412 to +544). The transcript start site is at position +1. The putative CAAT and TATA boxes are at −107 and −34. A putative poly (dA) site is at +785 (Skriver et al. (1992)).

5. FIG. 5 is the nucleotide sequence of the preferred embodiment of the present invention, i.e. a 787 bp fragment of the Ltp1 gene promoter. The same commentary for FIG. 3 is equally applicable here.

Figure 6:
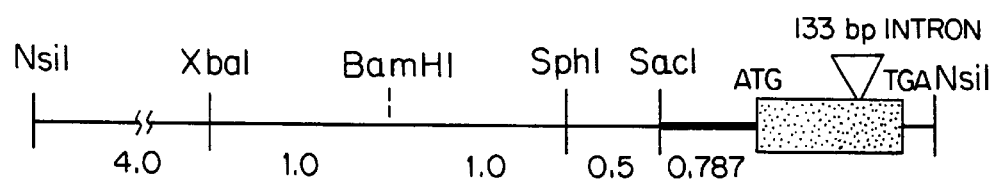
FIG. 6 is a linear map of the Ltp1.787-GN construct showing additional sequence information.

6. FIG. 6 is an outline of the Ltp1 genomic clone containing the Ltp1 structural gene (shaded box) and the promoter fragment fused to the GUS gene (black box) used to transform rice. Also indicated are the extensions of the Ltp1 fragment described in Linnestad et al. (1991) and Skriver et al. (1992). The figures used represent DNA fragment lengths in kb. The total length of the genomic clone is in the order of 8.1 kb.

7. FIG. 7 helps explain how pLtp1.787-GN was constructed. In this regard, the following fragments were sequentially cloned into the vector Bluescript KS⁻: firstly the 787 bp SacI/BcI fragment of the Ltp1 gene promoter was cloned into the SacI/BcII site of the vector; and secondly a GUS-Nos Terminator on 2150 bp SmaI/EcoRI fragment derived from pBI101 was cloned into SmaI/EcoRI downstream of the Ltp1 promoter.

Figure 8:
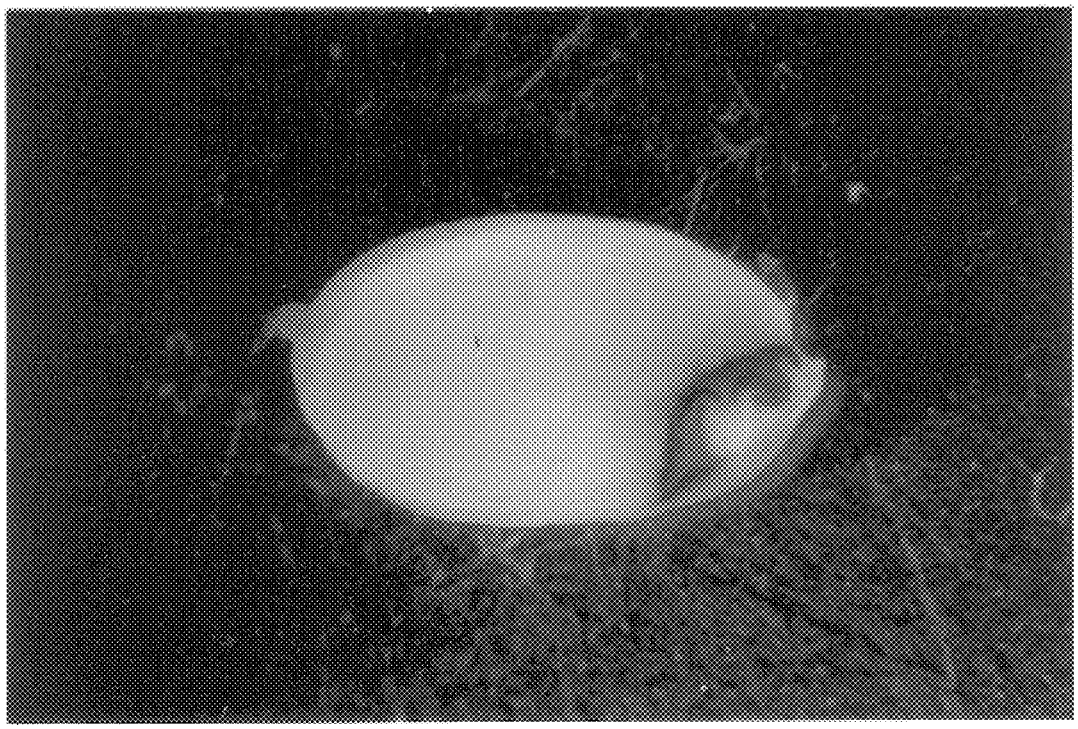
FIG. 8 is a longitudinal section of a developing rice grain post expression of the modified Ltp1 gene promoter.

8. FIG. 8 is a longitudinal section of a 30 day old transgenic rice grain showing transcriptional activity of the construct of FIG. 7 (i.e. pLtp1.787-GN) containing the promoter of FIG. 5. It is to be noted that transcriptional activity is achieved in the scutellar epithelial layer, as denoted by the blue staining.

Figure 9:
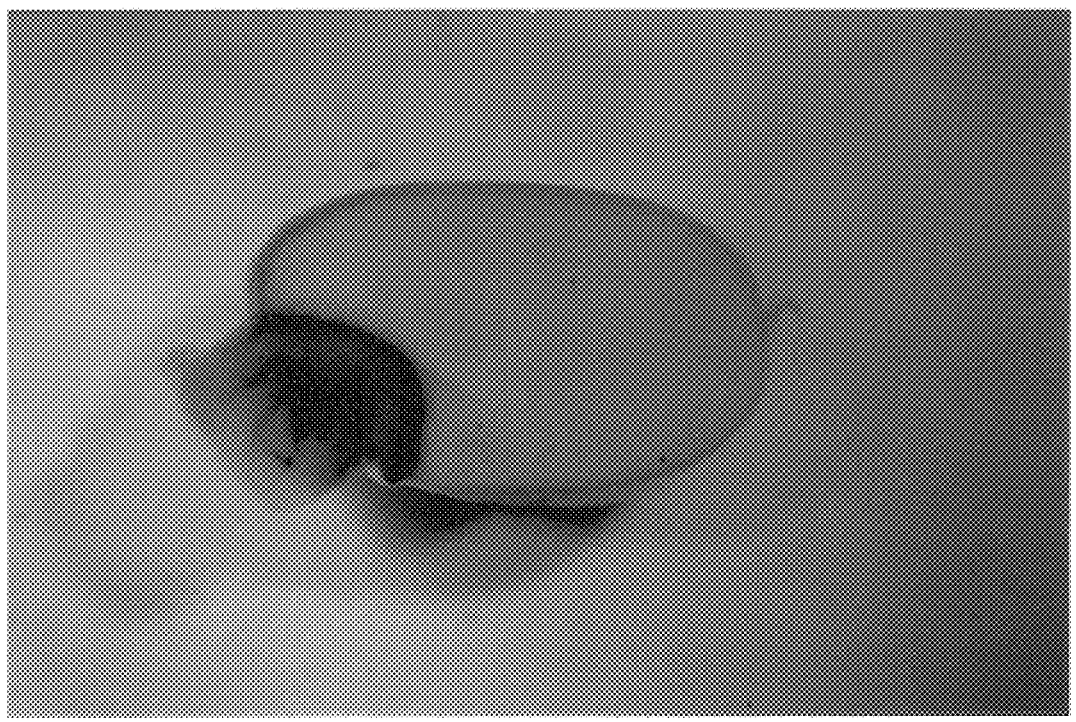
FIG. 9 is a longitudinal section of a mature germinating rice grain post expression of the modified Ltp1 gene promoter.

9. FIG. 9 is a longitudinal section of a mature germinating transgenic rice grain showing transcriptional activity of the construct of FIG. 7 (i.e. pLtp1.787-GN) containing the promoter of FIG. 5.

It is to be noted that transcriptional activity is achieved in the scutellar epithelial layer. Transcriptional activity is also observed in the shoot epithelial layer and in the aleurone layer. However, the extent of expression in the last two tissue types is not as pronounced as that in the scutellar epithelial layer.

However, more importantly, with the transgenic rice transcriptional activity is observed in the vascular tissue of the germinating seedling and the vascular tissue of the root and stem.

C. SUMMATION

The Examples relate to the isolation of and to the use of a 787 bp fragment of the promoter for the barley Ltp1 gene, which encodes a 10 kDa nsLTP. The gene was isolated by the use of a cDNA from a differential screening experiment in which the positive probe was constructed from aleurone cell poly (A) rich RNA, and the negative probe from the starchy endosperm of immature grains.

A construct comprising the Ltp1 gene promoter fragment and a GOI (in this case GUS) was stably inserted into rice protoplasts.

Expression and in situ analysis for the wild type gene promoter demonstrated that the Ltp1 transcript is expressed in high levels only in the aleurone cells in developing barley caryopsis. This expression continued in germinating grains and also in plantlets and mature plants.

However, for transgenic cereals, especially rice, even though there is some expression in the aleurone layer for the modified Ltp1 gene promoter it is, however, not as pronounced as that in each of the epithelial cells of the scutellum, the epidermal cells of the coleoptile and the vascular strands of the embryo of developing caryopsis (or grain).

This result is completely unexpected as it shows that a modified Ltp1 promoter can function differently in transgenic cereals, especially rice, than the wild-type Ltp1 gene in barley.

Expression and histochemical analysis for the transgenic rice demonstrated that the Ltp1 transcript is expressed in high levels in the scutellar epithelial tissue and vascular tissue, especially of a germinating rice seedling and a developing rice grain and a rice plant (e.g. in the root, leaves and stem). This expression continued in germinating grains and also in plantlets and mature plants.

Importantly, for rice, expression is observed in the vascular tissue of the germinating seedling and the vascular tissue of the root and stem.

This result is completely unexpected in view of the expression pattern of wild-type Ltp1 gene in barley.

Using the 787 bp promoter fragment in particle bombardments of developing barley caryopsis, we obtained activity (blue spots) in the epithelium layer of the scutellum.

The results therefore indicate that the modified Ltp1 gene promoter directs expression of a GOI predominantly in the aleurone cells of developing caryopsis, particularly for barley, or the scutellar epithelial tissue or vascular tissue of a germinating seedling or a developing grain or a plant (e.g. in the root, leaves and stem) particularly for rice.

The modified Ltp1 gene promoter therefore represents a valuable tool for the expression of GOIs in the aleurone layer of developing caryopsis, in particular developing barley caryopsis.

Moreover, the modified Ltp1 gene promoter represents a valuable tool for the expression of GOIs in the scutellar epithelial cells and vascular cells of germinating seedlings or developing grain, in particular developing or germinating rice seedlings or grain. The epithelial or vascular expression is of particular benefit because the 787 bp LTP1 gene fragment can be used to express antisense α-amylase in the scutellar epithelial layer in order to reduce or to prevent damage due to preharvest sprouting or to introduce or enhance pathogen resistance.

One possible reason for the expression activity of the modified Ltp1 gene promoter of the present invention may be the absence of "silencer" elements in the modified gene promoter which prevent expression of the wild type gene in, for example, the scutellar epithelial layer and vascular cells. Accordingly, the term "modified" (as defined above) could include removal of any silencer elements from the wild type Ltp1 gene promoter.

Studies with the modified Ltp1 gene promoter having deletions from and between the myb and myc sites when fused to GN showed that the relative activity of the deleted modified Ltp1 gene promoter was less (in some cases 70% less) than the modified Ltp1 gene promoter which contains the myb and myc sites. Therefore, it is believed that the presence of the myb and myc sites are important for even higher levels of expression of the modified Ltp1 promoter in at least protoplasts of at least rice.

Accordingly the present invention also covers a method of enhancing the in vivo expression of a GOI in at least the aleurone layer of a developing caryopsis or in at least the scutellar epithelial tissue or vascular tissue of a germinating seedling or a developing grain or a plant preferably of an embryo of a developing monocotyledon grain or caryopsis, comprising stably inserting into the genome of those cells a DNA construct comprising a modified Ltp1 gene promoter and a GOI, wherein in the formation of the construct the modified Ltp1 gene promoter is ligated to the GOI in such a manner that each of the myb site and the myc site in the modified Ltp1 gene promoter is maintained substantially intact.

The present invention also covers the use of a myb site and a myc site in a modified Ltp1 gene promoter to enhance in vivo expression of a GOI in at least the aleurone layer of a developing caryopsis or in at least the scutellar epithelial tissue or vascular tissue of a germinating seedling or a developing grain or a plant, preferably of an embryo of a developing monocotyledon caryopsis or grain, wherein the modified Ltp1 gene promoter and the GOI are integrated into the genome of the monocotyledon.

Each of these aspects is applicable to the combination expression system.

D. CONCLUSIONS VIS-A-VIS THE SPECIFIC EXAMPLES

1. The barley Ltp1 gene encodes a protein homologous to the 10 kDa wheat lipid transfer protein.
2. The wild type Ltp1 gene promoter is expressed in developing barley aleurone cells.
3. The modified Ltp1 gene promoter is transiently expressed in developing barley scutellar epithelial cells after particle bombardment.
4. The modified Ltp1 gene promoter directs expression of the GUS-reporter gene in the scutellar epithelial cells of developing transgenic rice grains. However, more pronounced expression is observed in the vascular tissue of germinating seedlings and the root and stem of the transgenic rice plant.
5. The modified Ltp1 gene promoter contains sequence elements implicated in the transcriptional control of cereal endosperm specific genes.
6. The modified Ltp1 gene promoter contains myb and myc sequence elements that are implicated in the level of transcription in cereal endosperm.

Other modifications of the present invention will be apparent to those skilled in the art without departing from the scope of the invention.

REFERENCES

Bosnes, M., Weideman, F. and Olsen, O.-A. (1992) Endosperm differentiation in barley wild-type and sex mutants. *Plant J.* 2, 661–674.

De Silva et al. 1992 WO 92/18634

Dellaporta, S. L., Greenblatt, I., Kermicle, J. L., Hick, J. B. and Wessler, S. (1988) Molecular cloning of the R-nj allelel by transposon tagging with Ac. In *Chromosome structure and function: Impact of new concepts*, 18th Stadler Genetics Symposium (Gustafson, J. P. and Appels, R., eds.), New York: Plenum Press, pp. 263–282.

Dieryck, W., Gautier, M.-F., Lullien, V. and Joudrier, P. (1992) Nucleotide sequence of a cDNA encoding a lipid transfer protein from wheat (*Triticum durum* Desf.). *Plant Mol. Biol.* 19, 707–709.

Fincher, G. B. (1989) Molecular and cellular biology associated with endosperm mobilization in germinating cereal grains. *Annu. Rev. Plant Physiol. Plant Mol. Biol.* 40, 305–346.

Fleming, A. J, Mandel, T., Hofmann, S., Sterk, P., de Vries, S. C., and Kuhlemeier, C. (1992) Expression pattern of a tobacco lipid transfer protein gene within the shoot apex. *Plant J.* 2, 855–862.

Gordon-Kanun, W. J., Spencer, T. M., Mangano, M. L., Adams, T. R., Daines, R. J., Start, W. G., O'Brien, J. V., Chambers, S. A., Adams, W. R., Willetts, N. G., Rice, T. B., Mackey, C. J., Krueger, R. W., Kausch, A. P. and Lemaux, P. G. (1990) Transformation of maize cells and regeneration of fertile transgenic plants. *Plant Cell* 2, 603–618.

Jacobsen, J. V., Knox, R. B. and Pyliotis, N. A. (1971) The structure and composition of aleurone grains in the barley aleurone layer. *Planta* 101, 189–209.

Jakobsen, K., Klemsdal, S., Aalen, R., Bosnes, M., Alexander, D. and Olsen, O.-A. (1989) Barley aleurone cell development: molecular cloning of aleurone-specific cDNAs from immature grains. *Plant Mol. Biol.* 12, 285–293.

Jefferson, R. A. (1987) Assaying chimeric genes in plants: the GUS gene fusion system. *Plant Mol. Biol. Rep.* 5, 387–405.

Kader, J.-C., Julienne, M. and Vergnolle, C. (1984) Purification and characterisation of a spinach-leaf protein capable of transferring phospholipids from liposomes to mitochondria or chloroplasts. *Eur. J. Biochem.* 139, 411–416.

Karrer, E. J., Litts, J. C and Rodriguez, R. L. (1991) Differential expression of α-amylase genes in germinating rice and barley seeds. *Plant Mol. Biol.* 16, 797–805.

Klemsdal, S. S., Hughes, W., Lonneborg, A., Aalen, R. and Olsen, O.-A. (1991) Primary structure of a novel barley gene differentially expressed in immature aleurone layers. *Mol. Gen. Genet* 228 9–16.

Koltunow, A. M., Truettner, J., Cox, K. H., Wallroth, M. and Goldberg, R. B. (1990) Different temporal and spatial expression patterns occur during anther development. *Plant Cell* 2, 1201–1224.

Kosugi, S., Ohashi, Y., Nakajima, K. and Arai, Y. (1990) An improved assay for β-glucuronidase in transformed cells: methanol almost completely suppresses a putative endogenous β-glucuronidase activity. *Plant Sci.* 70, 133–140.

Kvaale, A. and Olsen, O.-A. (1986) Rates of cell division in developing barley endosperms. *Ann. Bot.* 57, 829–833.

Lea, R., Tommerup, H., Svendsen, I. and Mundy, J. (1991) Biochemical and molecular characterization of three barley seed proteins with antifungal properties. *J. Biol. Chem.* 266, 1564–73.

Linnestad, C., Lonneborg, A., Kalla, R. and Olsen, O.-A. (1991) The promoter of a lipid transfer protein gene expressed in barley aleurone cells contains similar Myb and Myc recognition sites as the maize Bz-McC allele. *Plant Physiol.* 97, 841–843.

McClintock, B. (1978) Development of the maize endosperm as revealed by clones. In *The clonal basis of development* (Subtelny, S. and Sussex, I. M., eds.), New York: Academic Press, pp.217–237.

Monnet, F.-P. (1990) Ph.D thesis. Universite des Sciences et Techniques du Languedoc, Montpellier, France, pp. 121.

Mundy, J. and Rogers, J. (1986) Selective expression of a probable amylase/protease inhibitor in barley aleurone cells: comparison to the barley amylase/subtilisin inhibitor. *Planta* 169, 51–62.

Murashige, T., and Skoog, F. (1962) A revised medium for rapid growth and bioassays with tobacco tissue cultures. *Physiol. Plant.* 15, 473–497.

Old & S. B. Primrose (1993) *Principles of Gene Manipulation—An Introduction to Genetic Engineering* 4th Edition. Pub. Blackwell Scientific Publications. Pages 360–363.

Olsen, O.-A., Jakobsen, K. S. and Schmelzer, E. (1990) Development of barley aleurone cells: temporal and spatial patterns of accumulation of cell specific mRNAs. *Planta* 181 462–466

Olsen, O.-A., Potter, R. H. and Kalla, R. (1992) Histo-differentiation and molecular biology of developing cereal endosperm. *Seed Sci. Res.* 2, 117–131.

Paz-Ares, J., Ghosal, D., Wienand, U., Peterson, P. A. and Saedler, H. (1987) The regulatory c1 locus of *Zea mays* encodes a protein with homology to myb proto-oncogene products and with structural similarities to transcriptional activators. *EMBO J.* 6, 3553–3558.

Schmelzer, E., Jahnen, W. and Hahlbrock, K. (1988) In situ localization of light-induced chalcone synthetase mRNA, chalcone synthetase, and flavonoid end products in epidermal cells of parsley leaves. *Proc. Natl. Acad. Sci. U.S.A* 85, 2989–2993.

Shah et al. [1986] *Science* 233 478–81

Shimamoto, K., Terada, R., Izawa, T. and Fujimoto, H. (1989) Fertile transgenic rice plants regenerated from transformed protoplasts. *Nature* 338, 274–276.

Skriver, K., Leah, R., Müller-Uri, F., Olsen, F.-L. and Mundy, J. (1992) Structure and expression of the barley lipid transfer gene Ltp1. *Plant Molecular Biology* 18 585–589.

Slakeski, N. and Fincher, G. B. (1992) Developmental regulation of (1-3,1-4)-b-glucanase gene expression in barley. *Plant Physiol.* 99, 1226–1231.

Smith, L. M., Handley, J., Li, Y., Martin, H., Donovan, L. and Bowles, D. J. (1992) Temporal and spatial regulation of a novel gene in barley embryos. *Plant Mol. Biol.* 20, 255–266.

Somssich, I. E., Schmelzer, E., Kawalleck, P. and Hahlbrock, K. (1988) Gene structure and in situ transcript localization of the pathogenesis-related protein 1 in parsley. *Mol. Gen. Genet.* 213, 93–98.

Sossountzov, L., Riuz-Avila, L., Vignois, F., Jolliot, A., Arondel, V., Tchang, F., Grosbois, M., Guerbette, F., Miginiac, E., Delsney, M., Puigdomenech, P. and Kader, J.-C. (1991) Spatial and temporal expression pattern of a maize lipid transfer protein gene. *Plant Cell* 3, 923–933.

Sterk, P., Booij, H., Schellekens, G. A., Van Kammen, A. and De Vries, S. C. (1991) Cell-specific expression of the carrot EP2 lipid transfer protein gene. *Plant Cell* 3, 907–921.

Thoma, S., Kaneko, Y. and Sommerville, C. (1993) A non-specificlipid transfer protein from Arabidopsis is a cell wall protein. *The Plant Journal* 3(3), 427–436.

Watanabe, S. and Yamada, M. (1986) Purification and characterization of a non-specific lipid transfer protein from germinated castor bean endosperms which transfers phospholipids and galactolipids. *Biochim. Biophys. Acta.* 876, 116–123.

We claim:

1. A gene promoter, comprising:
    a nucleic acid sequence shown as SEQ ID NO: 1;
    wherein the gene promoter is a modified Ltp1 gene promoter;
    and when gene promoter is fused with a gene of interest and is integrated within a plant material's genomic DNA;
    said gene promoter induces expression of the gene of interest in the scutellar epithelial tissue or the vascular tissue of a germinating seedling or a developing grain or a plant.

2. The gene promoter according to claim 1 wherein the gene promoter is obtained from plasmid NCIMB 40609.

3. The gene promoter according to claim 1 wherein the plant is a cereal selected from the group consisting of a rice, a maize, a wheat and a barley.

4. A construct, comprising:
    a GOI and a modified Ltp1 gene promoter;
    wherein the gene promoter comprises the nucleic acid sequence shown as SEQ ID NO: 1;
    wherein the construct is integrated within a plant material's genomic DNA; and
    wherein the gene promoter induces expression of the gene of interest when fused to the gene promoter in the scutellar epithelial tissue or the vascular tissue of a germinating seedling or a developing grain or a plant.

5. The construct according to claim 4 wherein the seedling or grain or plant is selected from the group consisting of a rice, a maize, a wheat, and a barley.

6. The gene promoter according to claim 3 wherein the cereal is a rice.

7. The gene promoter according to claim 3 wherein the cereal is a maize.

8. The gene promoter according to claim 3 wherein the cereal is a wheat.

9. The gene promoter according to claim 3 wherein the cereal is a barley.

10. The construct according to claim 5 wherein the seedling or grain or plant is a rice.

11. The construct according to claim 5 wherein the seedling or grain or plant is a maize.

12. The construct according to claim 5 wherein the seedling or grain or plant is a wheat.

13. The construct according to claim 5 wherein the seedling or grain or plant is a barley.

14. A process of expressing a gene of interest in the scutellar epithelial tissue or vascular tissue of a plant material, comprising the steps of:
    fusing a gene of interest to a modified Ltp1 gene promoter having the nucleic acid sequence shown as SEQ ID NO: 1;
    integrating the gene promoter and the gene of interest within a plant material's genomic DNA such that the promoter induces expression of the gene of interest in the scutellar epithelial or vascular tissue of a germinating seedling or a developing grain or a plant; and
    inducing the gene of interest in the scutellar epithelial or vascular tissue of a germinating seedling, or a developing grain or a plant.

15. The process according to claim 14 wherein the seedling, grain, or plant is a rice.

16. The process according to claim 14 wherein the seedling, grain, or plant is a maize.

17. The process according to claim 14 wherein the seedling, grain or plant is a wheat.

18. The process according to claim 14 wherein the seedling, grain or plant is a barley.

19. A developing cereal grain, comprising:
    a construct comprising a gene of interest and a gene promoter;
    wherein the gene promoter comprises the nucleic acid sequence shown as SEQ ID NO: 1;
    wherein the gene promoter is a modified Ltp1 gene promoter;
    wherein the construct is integrated within a plant material's genomic DNA; and
    wherein the gene promoter induces expression of the gene of interest when fused to the gene promoter in the scutellar epithelial tissue or the vascular tissue of a germinating seedling or a developing grain or plant.

20. The cereal grain according to claim 19 comprising a rice.

21. The cereal grain according to claim 19 comprising a maize.

22. The cereal grain according to claim 19 comprising a wheat.

23. The cereal grain according to claim 19 comprising a barley.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 787 residues
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Barley (xi) SEQUENCE DESCRIPTION: SEQ ID NO:1:

```
GAGCTCCAAG GCATCACCAA GCTTCTATGA CGCCAAAACA TCCAAGAAAG ATATGTACTA      60

GGATACCAAG CACCCAAGAG TAAACGGAGG AAGTATAATA TAAGGCCCTG TTTGATAACA     120

AAGTAGTAAA AAAACTAAAG TATTAAAAAC TGCAGTAATT TTACGTGTAG ATAGAAAATA     180

CCATGGTTTT AATATAATAA TATTTTTTGC AGTATTCACA ATGTAGAGAA ACTGTTTGAT     240

TACGCCACAT ATTACTGCAG TTTAGATCGA GCAAGTACAC GGGAAGAAGA TAACGACGTC     300

CCACCCCTTC TTTTCGCCTT CTCTGTTTTT TAAAAAGAGG TCTGGGGTTA GTTTTTTCAA     360

TACTGCAGTT TTAAAATCAC AATTCTTAGA GGCAACCAAA CACCTCATTG TAAATAAAAC     420

TATGATAATC TCCAAAACTG CAGTATTCTA AAAATACTAC AAAAATTCTT TGTTATCAAA     480

CAGGGCCTAA GGAGTTAAAA AAATTTAGCC GTAACTGAGA CTCGGCGAGG CACCAGCAGC     540

TAGCAGTCAT CAACACTTGA TGGTTGGCAA AGCCGAGTCG ACGTGTCGCG GGGCTCGGCC     600

TGAGCGGGAG ATACAATCTG TTCTCCAGTA ACCCCGTCGA TTTGGCCCGC CGACTAAAGC     660

ATCCAGGCAT CTCTCGCTCG AACCCCTATT TAAGCCCCTC CATTCCTCCC AACATTCTCC     720

ACACCTCCAC GAGTTGCTCA TCACTAGCTA GTACGTTGTA CTGTTAGCTA CAGATTAAGA     780

AGTGATC                                                               787
```

(2) INFORMATION FOR SEQ ID NO:2:

(i) SEQUENCE CHARACTERISTICS:
        (A) LENGTH:  807 residues
        (B) TYPE: nucleic acid
        (C) STRANDEDNESS: double
        (D) TOPOLOGY: linear (ii) MOLECULE TYPE:  Genomic DNA (vi) ORIGINAL SOURCE:
        (A) ORGANISM: Barley (xi) SEQUENCE DESCRIPTION: SEQ ID NO:2:

```
GATCTCGATG TGTAGTCTAC GAGAAGGGTT AACCGTCTCT TCGTGAGAAT AACCGTGGCC      60

TAAAAATAAG CCGATGAGGA TAAATAAAAT GTGGTGGTAC AGTACTTCAA GAGGTTTACT     120

CATCAAGAGG ATGCTTTTCC GATGAGCTCT AGTAGTACAT CGGACCTCAC ATACCTCCAT     180

TGTGGTGAAA TATTTTGTGC TCATTTAGTG ATGGGTAAAT TTTGTTTATG TCACTCTAGG     240

TTTTGACATT TCAGTTTTGC CACTCTTAGG TTTTGACAAA TAATTTCCAT TCCGCGGCAA     300

AAGCAAAACA ATTTTATTTT ACTTTTACCA CTCTTAGCTT TCACAATGTA TCACAAATGC     360

CACTCTAGAA ATTCTGTTTA TGCCACAGAA TGTGAAAAAA AACACTCACT TATTTGAAGC     420

CAAGGTGTTC ATGGCATGGA AATGTGACAT AAAGTAACGT TCGTGTATAA GAAAAAATTG     480

TACTCCTCGT AACAAGAGAC GGAAACATCA TGAGACAATC GCGTTTGGAA GGCTTTGCAT     540

CACCTTTGGA TGATGCGCAT GAATGGAGTC GTCTGCTTGC TAGCCTTCGC CTACCGCCCA     600

CTGAGTCCGG GCGGCAACTA CCATCGGCGA ACGACCCAGC TGACCTCTAC CGACCGGACT     660

TGAATGCGCT ACCTTCGTCA GCGACGATGG CCGCGTACGC TGGCGACGTG CCCCCGCATG     720

CATGGCGGCA CATGGCGAGC TCAGACCGTG CGTGGCTGGC TACAAATACG TACCCCGTGA     780

GTGCCCTAGC TAGAAACTTA CACCTGC                                         807
```

(2) INFORMATION FOR SEQ ID NO:3:

(i) SEQUENCE CHARACTERISTICS:
        (A) LENGTH:  1487 residues
        (B) TYPE: nucleic acid
        (C) STRANDEDNESS: double
        (D) TOPOLOGY: linear (ii) MOLECULE TYPE:  Genomic DNA (vi) ORIGINAL SOURCE:
        (A) ORGANISM: Barley (x) PUBLICATION INFORMATION:
        (A) AUTHORS:
            Linnestad, Casper
            Lonneborg, Anders
            Kalla, Roger
            Olsen, Odd-Arne
        (B) TITLE:  Promoter of a Lipid Transfer Protein Gene
            Expressed in Barley Aleurone Cells Contains
            Similar myb and myc Recognition Sites as the Maize
            Bz-McC Allele
        (C) JOURNAL:  Plant Physiol.
        (D) VOLUME:97
        (F) PAGES: 842
        (G) DATE: 17.06.91

(xi) SEQUENCE DESCRIPTION: SEQ ID NO:3:

```
GAGCTCCAAG GCATCACCAA GCTTCTATGA CGCCAAAACA TCCAAGAAAG ATATGTACTA      60

GGATACCAAG CACCCAAGAG TAAACGGAGG AAGTATAATA TAAGGCCCTG TTTGATAACA     120

AAGTAGTAAA AAAACTAAAG TATTAAAAAC TGCAGTAATT TTACGTGTAG ATAGAAAATA     180
```

-continued

```
CCATGGTTTT AATATAATAA TATTTTTTGC AGTATTCACA ATGTAGAGAA ACTGTTTGAT      240

TACGCCACAT ATTACTGCAG TTTAGATCGA GCAAGTACAC GGGAAGAAGA TAACGACGTC      300

CCACCCCTTC TTTTCGCCTT CTCTGTTTTT TAAAAAGAGG TCTGGGGTTA GTTTTTTCAA      360

TACTGCAGTT TTAAAATCAC AATTCTTAGA GGCAACCAAA CACCTCATTG TAAATAAAAC      420

TATGATAATC TCCAAAACTG CAGTATTCTA AAAATACTAC AAAAATTCTT TGTTATCAAA      480

CAGGGCCTAA GGAGTTAAAA AAATTTAGCC GTAACTGAGA CTCGGCGAGG CACCAGCAGC      540

TAGCAGTCAT CAACACTTGA TGGTTGGCAA AGGCGAGTCG ACGTGTCGCG GGGCTCGGCC      600

TGAGCGGGAG ATACAATCTG TTCTCCAGTA ACCCCGTCGA TTTGGCCCGC CGACTAAAGC      660

ATCCAGGCAT CTCTCGCTCG AACCCCTATT TAAGCCCCTC CATTCCTCCC AACATTCTCC      720

ACACCTCCAC GAGTTGCTCA TCACTAGCTA GTACGTTGTA CTGTTAGCTA CAGATTAAGA      780

AGTGATC ATG GCC CGC GCT CAG GTA CTG CTC ATG GCC GCC GCC TTG GTG        829
        Met Ala Arg Ala Gln Val Leu Leu Met Ala Ala Ala Leu Val
        1               5                   10

CTG ATG CTC ACG GCG GCC CCG CGC GCT GCC GTG GCC CTC AAC TGC GGC        877
Leu Met Leu Thr Ala Ala Pro Arg Ala Ala Val Ala Leu Asn Cys Gly
15                  20                  25                  30

CAG GTT GAC AGC AAG ATG AAA CCT TGC CTG ACC TAC GTT CAG GGC GGC        925
Gln Val Asp Ser Lys Met Lys Pro Cys Leu Thr Tyr Val Gln Gly Gly
                35                  40                  45

CCC GGC CCG TCC GGC GAA TGC TGC AAC GGC GTC AGG GAT CTC CAT AAC        973
Pro Gly Pro Ser Gly Glu Cys Cys Asn Gly Val Arg Asp Leu His Asn
            50                  55                  60

CAG GCG CAA TCC TCG GGC GAC CGC CAA ACC GTT TGC AAC TGC CTG AAG       1021
Gln Ala Gln Ser Ser Gly Asp Arg Gln Thr Val Cys Asn Cys Leu Lys
65                  70                  75

GGG ATC GCT CGC GGC ATC CAC AAT CTC AAC CTC AAC AAC GCC GCC AGC       1069
Gly Ile Ala Arg Gly Ile His Asn Leu Asn Leu Asn Asn Ala Ala Ser
80                  85                  90

ATC CCC TCC AAG TGC AAT GTC AAC GTC CCA TAC ACC ATC AGC CCC GAC       1117
Ile Pro Ser Lys Cys Asn Val Asn Val Pro Tyr Thr Ile Ser Pro Asp
95                  100                 105                 110

ATC GAC TGC TCC AGG TGATTAAATT TACACTCATC CAGAGTGAAA TCTTTAAAAA       1172
Ile Asp Cys Ser Arg
                115

GAACTATATT TACGAACGGA GTGAGTATAT AGGAACATTC ATCCACGTAA AATTTGTTGA      1232

TATTAACATT AACACGCATG ATTGACCTGC AGG ATT TAC TGAGCGACGA                1281
                                    Ile Tyr

TCCGTCAAGC TGGTGCTCAG CTCATCGATC CACGTGGAGC TGAAGCGCGC AGCCTCTGTC     1341

CCTATGTAGT ATGGCTACCA GTTATGCCGA GTTTATGCTG AATAAGAACT CTCTCCTGTA     1401

CTCCTTTGGA GGAGATCAGT ATCTATGTAC GTGAGAGTTG AGAGTTTGTA CCATCGGCAC     1461

TCCCAGTGTT TATGGACTAT ATGCAT                                          1487
```

(2) INFORMATION FOR SEQ ID NO:4:

(i) SEQUENCE CHARACTERISTICS:
        (A) LENGTH: 117 residues
        (B) TYPE: amino acid
        (C) STRANDEDNESS: double
        (D) TOPOLOGY: linear (ii) MOLECULE TYPE:

(vi) ORIGINAL SOURCE:
        (A) ORGANISM: Barley (x) PUBLICATION INFORMATION:
            (A) AUTHORS:
                Linnestad, Casper
                Lonneborg, Anders
                Kalla, Roger
                Olsen, Odd-Arne
            (B) TITLE: Promoter of a Lipid Transfer Protein Gene
                Expressed in Barley Aleurone Cells Contains
                Similar myb and myc Recognition Sites as the Maize
                Bz-McC Allele
            (C) JOURNAL: Plant Physiol.
            (D) VOLUME:97
            (F) PAGES: 842
            (G) DATE: 17.06.91

(xi) SEQUENCE DESCRIPTION: SEQ ID NO:4:

```
Met Ala Arg Ala Gln Val Leu Leu Met Ala Ala Leu Val Leu Met
 1               5                  10                  15

Leu Thr Ala Ala Pro Arg Ala Ala Val Ala Leu Asn Cys Gly Gln Val
                20                  25                  30

Asp Ser Lys Met Lys Pro Cys Leu Thr Tyr Val Gln Gly Gly Pro Gly
            35                  40                  45

Pro Ser Gly Glu Cys Cys Asn Gly Val Arg Asp Leu His Asn Gln Ala
        50                  55                  60

Gln Ser Ser Gly Asp Arg Gln Thr Val Cys Asn Cys Leu Lys Gly Ile
65                  70                  75                  80

Ala Arg Gly Ile His Asn Leu Asn Leu Asn Asn Ala Ala Ser Ile Pro
                85                  90                  95

Ser Lys Cys Asn Val Asn Val Pro Tyr Thr Ile Ser Pro Asp Ile Asp
            100                 105                 110

Cys Ser Arg Ile Tyr
        115
```

(2) INFORMATION FOR SEQ ID NO:5:

(i) SEQUENCE CHARACTERISTICS:
        (A) LENGTH: 2874 residues
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Barley (x) PUBLICATION INFORMATION:
        (A) AUTHORS:
            Skriver, Karen
            Leah, Robert
            Muller-Uri, Frieder
            Olsen, Finn-Lok
            Mundy, John
        (B) TITLE: Structure and Expression of the Barley Lipid
            Transfer Protein Promoter of a Lipid Transfer Protein
            Gene Ltp1
        (C) JOURNAL: Plant Molecular Biology
        (D) VOLUME:18
        (F) PAGES: 587
        (G) DATE: 16.09.91

(xi) SEQUENCE DESCRIPTION: SEQ ID NO:5:

```
GTCCACAACTC ATGAGCATCA CGGAATGGCA TGAGTTGAAA TATAACTACA TTGCTCAAA     60

GCAACAAAAAG CACATTAGAA TCTTGAGCAT TGAGATAAGA GTTTTTCTCA TGCTCTAAA    120

TATATATTTTG AGAATCCTTT GGAGGAGAAA AATCCATATT TACAATTCGT TGTAAATTT    180

GAGTCCATGAT CCTAAAGAGA TTAAGCATGC GAATTACCCA AACATCAAAA TTTGTGCCA    240
```

```
TTGAAACTAAG AGTGTTAGAG AATCCTAATC CCCTAGTTGA CATACTTACT CTCTAGGTG    300

GTGAAACCTAA TAATGAGAGA TCTAGCTCTA ATACCAATTG AGAGGATGTG GATGTCGCC    360

TAGAGGGCGG TGAATAGGCG CTTTAAAATA ATTACGGTTT AGGCTCGAAC AAATGTGGA    420

ATAAAACTAAC GTTTCATTTG TCAAGCGCAA AACCTAAAAC AACTAGGCTC ACCTATGTG    480

CACCAACAACT TATGATAAGC AAGATAAAAA AACTAAGTGA TGGCAGAATA TATAACAAG    540

AAACAATATGG CTATCACAAA GTGAAGTGCA TAAGTAAACA GCTCGGGTAA GGGACAACC    600

GAGCCATGCGG AGACGACGAT GTATCCTCAA GTTCACACAC TTGCGGATGC TAATCTCCG    660

TTTGAAGCAGT GTGGAGGCAC AATCGTCCCC AAGAAGCCAC TAAGGCCACC GTAATCTCC    720

TCACGCCCTCG CACAATCGAA GATGTTGTGA TTCCACTAAG GGACCCTTGA GGGCAGTCA    780

CTGAACCCGTA TAAACATGGT TGGAACAATC TCCACGACTT AATTGGAGAC TCCCAACAA    840

CACCACGAACC TTCATCATAA CGAAATATGG CTTCGAGGTA ACCTCAAATG CTCGGGGCA    900

ATTTTTACAAC CTAATTGAAG ACCTCGACGC TTGCGTGGAG CTTTACACTA TAATGATTG    960

AGCTCCAAGGG CATCACCAAG CTTCTATGAC GCCAAAACAT CCAAGAAAGA TATGTACTA   1020

GGATACCAAGC ACCCAAGAGT AAACGGAGGA AGTATAATAT AAGGCCCTGT TTGATAACA   1080

AAGTAGTAAAA AAACTAAAGT ATTAAAAACT GCAGTAATTT TACGTGTAGA TAGAAAATA   1140

CCATGGTTTTA ATATAATAAT ATTTTTTGCA GTATTCACAA TGTAGAGAAA CTGTTTGAT   1200

TACGCCACATA TTACTGCAGT TTAGATCGAG CAAGTACACG GAAGAAGAT AACGACGTC    1260

CCACCCCTTCT TTTCGCCTTC TCTGTTTTTT AAAAAGAGGT CTGGGGTTAG TTTTTTCAA   1320

TACTGCAGTTT TAAAATCACA ATTCTTAGAG GCAACCAAA CACCTCATTG TAAATAAAAC   1380

TATGATAATC TCCAAAACTG CAGTATTCTA AAAATACTAC AAAAATTCTT TGTTATCAAA   1440

CAGGGCCTAA GGAGTTAAAA AAATTTAGCC GTAACTGAGA CTCGGCGAGG CACCAGCAGC   1500

TAGCAGTCAT CAACACTTGA TGGTTGGCAA AGGCGAGTCG ACGTGTCGCG GGGCTCGGCC   1560

TGAGCGGGAG ATACAATCTG TTCTCCAGTA ACCCCGTCGA TTTGGCCCGC CGACTAAAGC   1620

ATCCAGGCAT CTCTCGCTCG AACCCCTATT TAAGCCCCTC CATTCCTCCC AACATTCTCC   1680

ACACCTCCAC GAGTTGCTCA TCACTAGCTA GTACGTTGTA CTGTTAGCTA CAGATTAAGA   1740

AGTGATC ATG GCC CGC GCT CAG GTA CTG CTC ATG GCC GCC GCC TTG GTG    1789
        Met Ala Arg Ala Gln Val Leu Leu Met Ala Ala Ala Leu Val
         1               5                  10

CTG ATG CTC ACG GCG GCC CCG CGC GCT GCC GTG GCC CTC AAC TGC GGC    1837
Leu Met Leu Thr Ala Ala Pro Arg Ala Ala Val Ala Leu Asn Cys Gly
 15              20                  25                  30

CAG GTT GAC AGC AAG ATG AAA CCT TGC CTG ACC TAC GTT CAG GGC GGC    1885
Gln Val Asp Ser Lys Met Lys Pro Cys Leu Thr Tyr Val Gln Gly Gly
             35                  40                  45

CCC GGC CCG TCC GGC GAA TGC TGC AAC GGC GTC AGG GAT CTC CAT AAC    1933
Pro Gly Pro Ser Gly Glu Cys Cys Asn Gly Val Arg Asp Leu His Asn
                 50                  55                  60

CAG GCG CAA TCC TCG GGC GAC CGC CAA ACC GTT TGC AAC TGC CTG AAG    1981
Gln Ala Gln Ser Ser Gly Asp Arg Gln Thr Val Cys Asn Cys Leu Lys
         65                  70                  75

GGG ATC GCT CGC GGC ATC CAC AAT CTC AAC CTC AAC AAC GCC GCC AGC    2029
Gly Ile Ala Arg Gly Ile His Asn Leu Asn Leu Asn Asn Ala Ala Ser
     80                  85                  90

ATC CCC TCC AAG TGC AAT GTC AAC GTC CCA TAC ACC ATC AGC CCC GAC    2077
Ile Pro Ser Lys Cys Asn Val Asn Val Pro Tyr Thr Ile Ser Pro Asp
 95                 100                 105                 110
```

-continued

```
ATC GAC TGC TCC AGG TGATTAAATT TACACTCATC CAGAGTGAAA TCTTTAAAAA      2132
Ile Asp Cys Ser Arg
            115

GAACTATATT TACGAACGGA GTGAGTATAT AGGAACATTC ATCCACGTAA AATTTGTTGA     2192

TATTAACATT AACACGCATG ATTGACCTGC AGG ATT TAC TGAGCGACGA               2241
                                    Ile Tyr

TCCGTCAAGC TGGTGCTCAG CTCATCGATC CACGTGGAGC TGAAGCGCGC AGCCTCTGTC     2301

CCTATGTAGT ATGGCTACCA GTTATGCCGA GTTTATGCTG AATAAGAACT CTCTCCTGTA     2361

CTCCTTTGGA GGAGATCAGT ATCTATGTAC GTGAGAGTTG AGAGTTTGTA CCATCGGCAC     2421

TCCCAGTGTT TATGGACTAT ATGCATACAC CTCCTTCTGT GCTCAGTGTG TAACTTGTCT     2481

CTCTGTTTCC TCACGTTCGC GTCTCATATA ATAATTTACT TATGTGCTCT AGGATCGTAG     2541

TACAGTATCA TATATATACC TCTCTATGAA TTAGTTTACC GTAGACCGTA TGTTTCTTGA     2601

ATCTGGATGA AAATTACGGA TTCAAGCGTG CGTCCCGCAT ATAATAAGCT TGCTTACGGA     2661

TTCAAGCGTG CGTCACGCGG CTCAGTAGAT GATGAGGATA CTCGCTGCTG CATCTCTACA     2721

TCCCGCTCAT GAGCTGAGCT GAGCCCGGGT CCTCCCCCGC TCCGGCCCGC TGGCCACCCC     2781

GGCCGGCCGA CCCTCAAACA GCCTTCATGA CGAGCCGCCC GCCAGCAAGA TCTGTTGGCT     2841

CCTCCCCTGT CCGTCGTAGA GAAACCCAGC GCA                                  2874
```

(2) INFORMATION FOR SEQ ID NO:6:

(i) SEQUENCE CHARACTERISTICS:
       (A) LENGTH: 117 residues
       (B) TYPE: amino acid
       (C) STRANDEDNESS: double
       (D) TOPOLOGY: linear (ii) MOLECULE TYPE:

(vi) ORIGINAL SOURCE:
       (A) ORGANISM: Barley (x) PUBLICATION INFORMATION:
       (A) AUTHORS:
           Skriver, Karen
           Leah, Robert
           Muller-Uri, Frieder
           Olsen, Finn-Lok
           Mundy, John
       (B) TITLE: Structure and Expression of the Barley Lipid
           Transfer Protein Promoter of a Lipid Protein Gene Ltp1
       (C) JOURNAL: Plant Molecular Biology
       (D) VOLUME:18
       (F) PAGES: 587
       (G) DATE: 16.09.91

(xi) SEQUENCE DESCRIPTION: SEQ ID NO:6:

```
Met Ala Arg Ala Gln Val Leu Leu Met Ala Ala Ala Leu Val Leu Met
 1               5                  10                 15

Leu Thr Ala Ala Pro Arg Ala Ala Val Ala Leu Asn Cys Gly Gln Val
                20                  25                 30

Asp Ser Lys Met Lys Pro Cys Leu Thr Tyr Val Gln Gly Gly Pro Gly
            35                  40                  45

Pro Ser Gly Glu Cys Cys Asn Gly Val Arg Asp Leu His Asn Gln Ala
        50                  55                  60

Gln Ser Ser Gly Asp Arg Gln Thr Val Cys Asn Cys Leu Lys Gly Ile
65                  70                  75                  80

Ala Arg Gly Ile His Asn Leu Asn Leu Asn Asn Ala Ala Ser Ile Pro
                85                  90                  95
```

-continued

```
Ser Lys Cys Asn Val Asn Val Pro Tyr Thr Ile Ser Pro Asp Ile Asp
            100                 105                 110
Cys Ser Arg Ile Tyr
            115
```